United States Patent
O'Sullivan et al.

(10) Patent No.: US 8,110,593 B2
(45) Date of Patent: Feb. 7, 2012

(54) PHENOXYMETHYL IMIDAZOLINE DERIVATIVES AND THEIR USE AS PESTICIDES

(75) Inventors: Anthony Cornelius O'Sullivan, Stein (CH); Christoph Luethy, Basel (CH); Jurgen Harry Schaetzer, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 158 days.

(21) Appl. No.: 12/526,977

(22) PCT Filed: Jan. 18, 2008

(86) PCT No.: PCT/EP2008/000366
§ 371 (c)(1),
(2), (4) Date: Aug. 13, 2009

(87) PCT Pub. No.: WO2008/098657
PCT Pub. Date: Aug. 21, 2008

(65) Prior Publication Data
US 2010/0120881 A1    May 13, 2010

(30) Foreign Application Priority Data
Feb. 15, 2007  (EP) ................................. 07003189

(51) Int. Cl.
*A61K 31/4164* (2006.01)
*A61K 31/4196* (2006.01)
*C07D 233/54* (2006.01)
*C07D 249/08* (2006.01)

(52) U.S. Cl. ..................... 514/383; 548/300.1
(58) Field of Classification Search ............. 514/383; 548/300.1
See application file for complete search history.

(56) References Cited

U.S. PATENT DOCUMENTS

| 4,163,105 A * | 7/1979 | Wysong ................ 548/353.1 |
| 4,226,876 A | 10/1980 | Copp et al. |
| 4,228,175 A | 10/1980 | Boger et al. |
| 4,232,011 A | 11/1980 | Boger et al. |
| 4,233,306 A | 11/1980 | Boger et al. |
| 4,241,075 A * | 12/1980 | Boger et al. ................ 514/401 |
| 4,276,302 A * | 6/1981 | Brechbuhler et al. ......... 514/401 |
| 4,414,223 A | 11/1983 | Copp et al. |
| 5,128,361 A * | 7/1992 | Stark et al. ................ 514/401 |
| 2010/0120882 A1* | 5/2010 | Luethy et al. ................ 514/401 |
| 2011/0098331 A1* | 4/2011 | Luethy et al. ................ 514/401 |

FOREIGN PATENT DOCUMENTS

| DE | 2818367 | 4/1978 |
| DE | 2940167 A1 | 4/1980 |
| EP | 0011596 | 5/1980 |
| EP | 049797 | 4/1982 |
| EP | 0423802 | 4/1991 |
| EP | 1958508 | 8/2008 |
| FR | 2388496 | 11/1978 |
| GB | 2023603 | 1/1980 |
| GB | 1592649 | 7/1981 |
| GB | 1593276 | 7/1981 |
| JP | 51106739 | 3/1975 |
| WO | 2009036908 | 3/2009 |
| WO | 2009036909 | 3/2009 |
| WO | 2009060174 | 5/2009 |

OTHER PUBLICATIONS

Patani et al., Chem. Rev., 1996, 96(8), 3147-3176, esp. p. 3149.*
Moormann, Alan E., et al.: Potential Antisecretory Antidiarrheal, J. Med. Chem., 1990, 33:614-626.

* cited by examiner

*Primary Examiner* — Susannah Chung
(74) *Attorney, Agent, or Firm* — Rebecca Howard

(57) ABSTRACT

The present invention relates to imidazoline derivatives and their use as insecticidal, acaricidal, molluscicidal and nematocidal agents. The invention also extends to insecticidal, acaricidal, molluscicidal and nematicidal compositions comprising such imidazoline derivatives, and to methods of using such derivatives and/or compositions to combat and control insect, acarine, mollusc and nematode pests. In particular the present invention relates to imidazolines with alkyl, cycloalkyl, alkenyl, cycloalkenyl, alkynyl, aryl, heteroaryl or heterocyclyl substituents.

18 Claims, No Drawings

PHENOXYMETHYL IMIDAZOLINE DERIVATIVES AND THEIR USE AS PESTICIDES

This application is a 371 of International Application No. PCT/EP2008/000366 filed Jan. 18, 2008, which claims priority to EP 07003189.3 filed Feb. 15, 2007, the contents of which are incorporated herein by reference.

The present invention relates to imidazoline derivatives and their use as insecticidal, acaricidal, molluscicidal and nematocidal agents. The invention also extends to insecticidal, acaricidal, molluscicidal and nematicidal compositions comprising such imidazoline derivatives, and to methods of using such derivatives and/or compositions to combat and control insect, acarine, mollusc and nematode pests. In particular the present invention relates to imidazolines with alkyl, cycloalkyl, alkenyl, cycloalkenyl, alkynyl, aryl, heteroaryl or heterocyclyl substituents.

A number of imidazoline derivatives are known, for example, European Patent Application No. EP 0423802 describes aryloxyarylimidazolines for pharmaceutical use. Moormann et al., (1990 J Med Chem 33:614-626) describe 2-[(aryloxy)alkyl]imidazolines as potential antidiarrheals and disclose the compound 3-(4,5-dihydro-1H-imidazol-2-yl)-3-(2,6-dimethyl-phenoxy)-propan-1-ol, which is inactive as an antidiarrheal.

Aryloxyalkylimidazolines for use in combating ectoparasites and/or acarids are known in the prior art, see for example U.S. Pat. Nos. 5,128,361, 4,226,876, 4,414,223, DE 2818367, EP 0011596, U.S. Pat. Nos. 4,276,302, 4,232,011, 4,241,075, 4,233,306. However, all of these describe aryloxyalkylimidazolines wherein the alkyl moiety is unsubstituted.

Japanese Patent Application No. JP 51106739 describes specific aryloxymethyl-imidazolines with acaricidal and insecticidal activity.

We have now found further novel imidazoline derivatives, which have surprisingly good pesticidal activity, in particular surprisingly good insecticidal and/or acaricidal activity. Thus according to a first aspect of the invention there is provided a compound of formula (I):

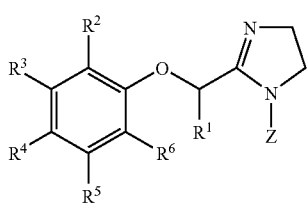

(I)

or salt or N-oxide thereof, wherein $R^1$ is (i) a substituted $C_{1-6}$ alkyl, (ii) an optionally substituted $C_{2-6}$ alkenyl, (iii) an optionally substituted $C_{3-6}$ cycloalkyl, (iv) an optionally substituted $C_{3-6}$ cycloalkenyl, or (v) an optionally substituted $C_{2-6}$ alkynyl; $R^2$ is methyl, ethyl, $C_{1-2}$ haloalkyl or halogen; $R^3$ is hydrogen, methyl, ethyl, $C_{1-2}$ haloalkyl or halogen; $R^4$ is hydrogen, methyl or halogen; $R^5$ is hydrogen, methyl or halogen; $R^6$ is hydrogen, methyl, ethyl, or halogen; Z is hydrogen, hydroxy, nitro, cyano, rhodano, formyl, G, G-S—, G-S—S—, G-A-, $R^7R^8N$—, $R^7R^8N$—S—, $R^7R^8N$-A-, G-O-A-, G-S-A-, $(R^{10}O)(R^{11}O)P(X)$—, $(R^{10}O)(R^{11}S)P(X)$—, $(R^{10}O)(R^{11})P(X)$—, $(R^{10}O)(R^{14}R^{15}N)P(X)$—, $(R^{11})(R^{14}R^{15}N)P(X)$—, $(R^{14}R^{15}N)(R^{16}R^{17}N)P(X)$—, G-N=CH—, G-O—N=CH—, N=N=CH—, or Z is a group of formula (II)

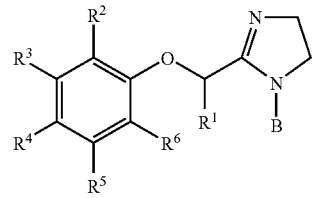

(II)

wherein B is S—, S—S—, S(O)—, —C(O)—, or $(CH_2)_n$—, n is an integer from 1 to 6 inclusive and $R^1$, $R^2$, $R^3$, $R^4$, $R^5$, and $R^5$ are as defined above; G is an optionally substituted $C_{1-10}$ alkyl, an optionally substituted $C_{2-6}$ alkenyl, an optionally substituted $C_{2-6}$ alkynyl, an optionally substituted $C_{3-7}$ cycloalkyl, an optionally substituted $C_{3-7}$ cycloalkenyl, an optionally substituted aryl, an optionally substituted heteroaryl or an optionally substituted heterocyclyl; A is S(O), $SO_2$, C(O) or C(S); $R^7$, $R^8$ and $R^9$ are each independently hydrogen or G; or $R^7$ and $R^8$ together with the N atom to which they are attached form a group $N=CR^{12}R^{13}$; or $R^7$ and $R^8$ together with the N atom to which they are attached form a five, six or seven-membered heterocyclic ring, which heterocyclic ring optionally contains one or two further heteroatoms selected from O, N or S, and is optionally substituted by one or two $C_{1-6}$ alkyl groups; $R^{19}$ and $R^{11}$ are each independently, $C_1$-$C_6$ alkyl, benzyl or phenyl, wherein the phenyl group is optionally substituted with halogen, nitro, cyano, $C_{1-3}$ alkyl, $C_{1-3}$ haloalkyl, $C_{1-3}$ alkoxy, $C_{1-3}$ haloalkoxy; $R^{12}$, $R^{13}$, $R^{14}$, $R^{15}$, $R^{16}$, and $R^{17}$ are each independently hydrogen or $C_1$-$C_6$ alkyl; and X is O or S, with the proviso that the compound of formula (I) is not 3-(4,5-dihydro-1H-imidazol-2-yl)-3-(2,6-dimethyl-phenoxy)-propan-1-ol.

For the avoidance of doubt, the term "compound" as used herein includes all salts and N-oxides of said compound.

The compounds of formula (I) may exist in different geometric or optical isomers or different tautomeric forms. One or more centres of chirality may be present, for example on the chiral carbon atom $CHR^1$ or a chiral carbon unit in the group G, or a chiral —S(O)— unit, in which case compounds of the formula (I) may be present as pure enantiomers, mixtures of enantiomers, pure diastereomers or mixtures of diastereomers.

There may be double bonds present in the molecule, such as C=C or C=N bonds, in which case compounds of formula (I) may exist as single isomers or mixtures of isomers. Centres of tautomerisation may be present. This invention covers all such isomers and tautomers and mixtures thereof in all proportions as well as isotopic forms such as deuterated compounds.

Suitable acid addition salts include those with an inorganic acid such as hydrochloric, hydrobromic, sulfuric, nitric and phosphoric acids, or an organic carboxylic acid such as oxalic, tartaric, lactic, butyric, toluic, hexanoic and phthalic acids, or sulphonic acids such as methane, benzene and toluene sulphonic acids. Other examples of organic carboxylic acids include haloacids such as trifluoroacetic acid.

N-oxides are oxidised forms of tertiary amines or oxidised forms of nitrogen containing heteroaromatic compounds. They are described in many books for example in "Heterocyclic N-oxides" by Angelo Albini and Silvio Pietra, CRC Press, Boca Raton, Fla., 1991.

Each alkyl moiety either alone or as part of a larger group (such as G, alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are suitably $C_1$ to $C_{10}$ alkyl groups, but are preferably $C_1$-$C_8$, even more preferably $C_1$-$C_6$ and most preferably $C_1$-$C_4$ alkyl groups.

Ring or chain forming alkylen, alkenylen and alkinyl groups can optionally be further substituted by one or more halogen, $C_{1-3}$ alkyl and/or $C_{1-3}$ alkoxy group.

When present, the optional substituents on an alkyl moiety (alone or as part of a larger group such as G, alkoxy, alkoxycarbonyl, alkylcarbonyl, alkylaminocarbonyl, dialkylaminocarbonyl) include one or more of halogen, nitro, cyano, rhodano, isothiocyanato, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{mo}$)alkoxy, tri($C_{1-4}$ alkylsilyl($C_{1-8}$)alkoxy, $C_{1-6}$ alkoxycarbonyl($C_{1-10}$)alkoxy, $C_{1-10}$ haloalkoxy, aryl($C_{1-4}$)-alkoxy (where the aryl group is optionally substituted), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, mercapto, $C_{1-10}$ alkylthio, $C_{1-10}$ haloalkylthio, aryl($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$)alkylsilyl($C_{1-6}$) alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be optionally substituted), tri($C_{1-4}$)alkylsilyl, aryldi($C_{1-4}$)alkylsilyl, ($C_{1-4}$)alkyldiarylsilyl, triarylsilyl, aryl ($C_{1-4}$)alkylthio($C_{1-4}$)alkyl, aryloxy($C_{1-4}$)alkyl, formyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)aminocarbonyl, N—($C_{1-3}$ alkyl)-N—($C_1$-3 alkoxy)aminocarbonyl, $C_{1-6}$ alkylcarbonyloxy, arylcarbonyloxy (where the aryl group is optionally substituted), di($C_{1-6}$)alkylaminocarbonyloxy, oximes and oximethers such as =NOalkyl, =NOhaloalkyl and =NOaryl (itself optionally substituted), aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$) alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the aikenyi moieties, where appropriate, can be of either the (E)- or (Z)-configuration. Examples are vinyl, allyl and propargyl. Alkenyl and alkynyl moieties can contain one or more double and/or triple bonds in any combination. It is understood, that allenyl and alkilinylalkenyl are included in these terms.

When present, the optional substituents on alkenyl or alkynyl include those optional substituents given above for an alkyl moiety.

In the context of this specification acyl is optionally substituted $C_{1-6}$ alkylcarbonyl (for example acetyl), optionally substituted $C_{2-6}$ alkenylcarbonyl, optionally substituted $C_{3-6}$ cycloalkylcarbonyl (for example cyclopropylcarbonyl, optionally substituted $C_{2-6}$ alkynylcarbonyl, optionally substituted arylcarbonyl (for example benzoyl) or optionally substituted heteroarylcarbonyl.

Halogen is fluorine, chlorine, bromine or iodine.

Haloalkyl groups are alkyl groups which are substituted with one or more of the same or different halogen atoms and are, for example, $CF_3$, $CF_2C_1$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

In the context of the present specification the terms "aryl", "aromatic ring" and "aromatic ring system" refer to ring systems which may be mono-, bi- or tricyclic. Examples of such rings include phenyl, naphthalenyl, anthracenyl, indenyl or phenanthrenyl. A preferred aryl group is phenyl. In addition, the terms "heteroaryl", "heteroaromatic ring" or "heteroaromatic ring system" refer to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidyl, triazinyl, thienyl, furyl, oxazolyl, isoxazolyl, 2,1,3-benzoxadiazole and thiazolyl.

The terms heterocycle and heterocyclyl refer to a non-aromatic preferably monocyclic or bicyclic ring systems containing up to 10 atoms including one or more (preferably one or two) heteroatoms selected from O, S and N. Examples of such rings include 1,3-dioxolane, oxetane, tetrahydrofuran, morpholine, thiomorpholin and piperazine.

When present, the optional substituents on heterocyclyl include $C_{1-6}$ alkyl and $C_{1-6}$ haloalkyl, an oxo-group (wherein one of the carbon atoms in the ring may be in the form of a keto group), as well as those optional substituents given above for an alkyl moiety.

Cycloalkyl includes cyclopropyl, cyclobutyl, cyclopentyl and cyclohexyl. Cycloalkylalkyl is preferentially cyclopropylmethyl. Cycloalkenyl includes cyclopentenyl and cyclohexenyl.

When present, the optional substituents on cycloalkyl or cycloalkenyl include $C_{1-3}$ alkyl as well as those optional substituents given above for an alkyl moiety.

Carbocyclic rings include aryl, cycloalkyl and cycloalkenyl groups. When present, the optional substituents on aryl or heteroaryl are selected independently, from halogen, nitro, cyano, rhodano, isothiocyanato, $C_{1-6}$ alkyl, $C_{1-6}$ haloalkyl, $C_{1-6}$ alkoxy-($C_{1-8}$)alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{6-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkyl-silyl($C_{1-6}$) alkoxy, $C_{1-6}$ alkoxycarbonyl($C_{1-10}$)alkoxy, $C_{1-10}$ haloalkoxy, aryl($C_{1-4}$)alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, mercapto, $C_{1-10}$ alkylthio, $C_{1-10}$ haloalkylthio, aryl($C_{1-4}$)alkylthio, $C_{3-7}$ cycloalkylthio (where the cycloalkyl group is optionally substituted with $C_{1-6}$ alkyl or halogen), tri($C_{1-4}$-alkylsilyl($C_{1-6}$) alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, ($C_{1-4}$) alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)-aminocarbonyl, N—($C_{1-3}$ alkyl)-N—($C_{1-3}$ alkoxy)aminocarbonyl, $C_{1-6}$ alkylcarbonyloxy, arylcarbonyloxy, di($C_{1-6}$)alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include aryl carbonyl amino (where the aryl group is substituted by $C_{1-6}$ alkyl or halogen), $C_{1-6}$alkoxycarbonylamino $C_{1-6}$alkoxycarbonyl-N—($C_{1-6}$) alkylamino, aryloxycarbonylamino (where the aryl group is substituted by $C_{1-6}$ alkyl or halogen), aryloxycarbonyl-N—($C_{1-6}$)alkylamino (where the aryl group is substituted by $C_{1-6}$ alkyl or halogen), arylsulphonylamino (where the aryl group is substituted by $C_{1-6}$ alkyl or halogen), arylsulphonyl-N—($C_{1-6}$)alkylamino (where the aryl group is substituted by $C_{1-6}$ alkyl or halogen), aryl-N—($C_{1-6}$)alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$alkylaminocarbonyl amino, di($C_{1-6}$) alkylaminocarbonyl amino, arylaminocarbonyl amino where the aryl group is substituted by $C_{1-6}$ alkyl or halogen), aryl-N—($C_{1-6}$)alkylaminocarbonylamino (where the aryl group is substituted by $C_{1-6}$ alkyl or halogen), $C_{1-6}$alkylaminocarbonyl-N—($C_{1-6}$)alkyl amino, di($C_{1-6}$)alkylaminocarbonyl-N—($C_{1-6}$)alkyl amino, arylaminocarbonyl-N—($C_{1-6}$)alkyl amino (where the aryl group is substituted by $C_{1-6}$ alkyl or halogen) and aryl-N—($C_{1-6}$)alkylaminocarbonyl-N—($C_{1-6}$)alkyl amino (where the aryl group is substituted by $C_{1-6}$ alkyl or halogen).

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, aryl, heteroaryl, amino, $C_{1-6}$ alkylamino, di($C_{1-6}$ alkylamino, aminocarbonyl, $C_{1-6}$ alkylaminocarbonyl, or di($C_{1-6}$ alkyl)aminocarbonyl.

Haloalkenyl groups are alkenyl groups which are substituted with one or more of the same or different halogen atoms.

It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, thiomorpholine and morpholine each of which may be substituted by one or two independently selected ($C_{1-6}$) alkyl groups.

Preferably the optional substituents on an alkyl moiety include one or more of halogen, nitro, cyano, $HO_2C$, $C_{1-10}$ alkoxy (itself optionally substituted by $C_{1-10}$ alkoxy), aryl ($C_{1-4}$)alkoxy, $C_{1-10}$ alkylthio, $C_{1-10}$ alkylcarbonyl, $C_{3-6}$ cycloalkylcarbonyl, $C_{1-10}$ alkoxycarbonyl, $C_{1-6}$ alkylaminocarbonyl, di($C_{1-6}$ alkyl)aminocarbonyl, ($C_{1-6}$)alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with ($C_{1-6}$) alkyl or halogen), $C_{3-7}$ cycloalkyloxy, $C_{6-7}$ cycloalkenyl, $C_{1-6}$ alkylsulfonyl, $C_{1-6}$ alkylsulfinyl, tri($C_{1-4}$)alkylsilyl, tri($C_{1-4}$) alkylsilyl($C_{1-6}$)alkoxy, aryldi($C_{1-4}$)alkylsilyl, ($C_{1-4}$)alkyldiarylsilyl and triarylsilyl.

Preferably the optional substituents on alkenyl or alkynyl include one or more of halogen, aryl and $C_{3-7}$ cycloalkyl.

A preferred optional substituent for heterocyclyl is $C_{1-3}$ alkyl. Preferably the optional substituents for cycloalkyl include halogen, cyano and $C_{1-6}$ alkyl.

The optional substituents for cycloalkenyl preferably include $C_{1-3}$ alkyl, halogen and cyano.

In particularly preferred embodiments of the invention, the preferred groups for $R^1$, $R^2$, $R^3$, $R^4$, $R^5$, $R^6$, and Z, in any combination thereof, are as set out below.

In certain embodiments, where $R^1$ is (i) a substituted $C_{1-6}$ alkyl, (ii) an optionally substituted $C_{2-6}$ alkenyl, (iii) an optionally substituted $C_{3-6}$ cycloalkyl, (iv) an optionally substituted $C_{3-6}$ cycloalkenyl, or (v) an optionally substituted $C_{2-6}$ alkynyl, said substitution in (i) and said optional substitution in any one of (ii) to (v) are each independently selected from one or more of: halogen; hydroxyl; nitro; cyano; rhodano; carboxy; formyl; formyloxy; formylamino; optionally substituted $C_{3-7}$ cycloalkyl, said substitution being selected from one or more of halogen, hydroxy, nitro, cyano, rhodano, $C_{1-3}$ alkyl, $C_{1-3}$ haloalkyl and $C_{1-3}$ alkoxy; optionally substituted $C_{3-7}$ cycloalkenyl, said substitution being selected from one or more of halogen, hydroxy, nitro, cyano, rhodano, $C_{1-3}$ alkyl, $C_{1-3}$ haloalkyl, and $C_{1-3}$ alkoxy; optionally substituted aryl, said substitution being selected from one or more of halogen, hydroxy, nitro, cyano, rhodano, $C_{1-3}$ alkyl, $C_{1-3}$ haloalkyl, $C_{1-3}$ alkoxy, $C_{1-3}$ haloalkoxy, $C_{1-3}$ alkylthio, $C_{1-3}$ alkylsulfinyl, $C_{1-3}$ alkylsulfonyl, $C_{1-3}$ haloalkylthio, and $C_{1-4}$ alkoxycarbonyl; optionally substituted heteroaryl, said substitution being selected from one or more of halogen, hydroxy, nitro, cyano, rhodano, $C_{1-3}$ alkyl, $C_{1-3}$ haloalkyl, $C_{1-3}$ alkoxy, $C_{1-3}$ haloalkoxy, $C_{1-3}$ alkylthio, $C_{1-3}$ alkylsulfinyl, $C_{1-3}$ alkylsulfonyl, $C_{1-3}$ haloalkylthio, $C_{1-3}$ alkoxycarbonyl, carbamoyl, $C_{1-4}$ alkylaminocarbonyl and di-$C_{1-4}$ alkylaminocarbonyl; optionally substituted heterocyclyl, said substitution being selected from one or more of halogen, hydroxy, nitro, cyano, rhodano, $C_{1-3}$ alkyl, $C_{1-3}$ haloalkyl, and $C_{1-3}$ alkoxy; G-O—; G-S—; G-A-; G-A-O—; G-A-S—; $R^7R^8N$—; $R^7R^8N$-A-; G-O-A-; G-S-A-; G-A-$NR^9$—; $R^7R^8N$-A-$NR^9$—; and G-O-A-$NR^9$—.

In preferred embodiments when $R^1$ is substituted $C_{1-6}$ alkyl the substitution will be selected from one or more of: halogen, hydroxyl, cyano, optionally substituted $C_{3-6}$ cycloalkyl (said substitution being selected from halogen, cyano, $C_{1-3}$ haloalkyl and $C_{1-3}$ alkoxy), optionally substituted pyridyl, pyrimidinyl, furyl or thienyl (said substitution being selected from halogen, cyano, $C_{1-3}$ alkyl, $C_{1-3}$ haloalkyl and $C_{1-3}$ alkoxy), optionally substituted tetrahydrofuryl, tetrahydropyranyl or 1,3-dioxolanyl (said substitution being selected from $C_{1-3}$ alkyl and $C_{1-3}$ alkoxy), $C_{1-3}$ alkoxy, $C_{1-3}$ haloalkoxy, allyloxy, propargyloxy, $C_{1-3}$ alkylthio, $C_{1-3}$ alkylsulfinyl, $C_{1-3}$ alkylsulfonyl, formyl, $C_{1-3}$ alkylcarbonyl, cyclopropylcarbonyl, $C_{1-3}$ haloalkylcarbonyl, $C_{1-3}$ alkoxycarbonyl, $C_{1-3}$ alkylthiocarbonyl, aminocarbonyl, $C_{1-3}$ alkylaminocarbonyl, N,N-di-($C_{1-3}$alkyl)aminocarbonyl, amino, $C_{1-3}$ alkylamino, di($C_{1-3}$ alkylamino, formylamino, $C_{1-3}$ alkylcarbonylamino, $C_{1-3}$ haloalkylcarbonylamino, $C_{1-3}$ alkylsulfonylamino, $C_{1-3}$ haloalkylsulfonylamino, $C_{1-3}$ alkylcarbonyloxy, $C_{1-3}$ haloalkylcarbonyloxy, cyclopropylcarbonyloxy, benzoyloxy, $C_{1-3}$ alkoxycarbonylamino, $C_{1-3}$ alkoxycarbonyloxy and $C_{1-3}$ alkylcarbonylthio.

In other preferred embodiments where $R^1$ is an optionally substituted $C_{2-6}$ alkenyl said substitution is selected from one or more of: halogen, cyano, optionally substituted $C_{3-6}$ cycloalkyl, (said substitution being selected from halogen and $C_{1-3}$ alkoxy), $C_{1-3}$ alkoxy, $C_{1-3}$ haloalkoxy, $C_{1-3}$ alkylthio, $C_{1-3}$ haloalkylthio, $C_{1-3}$ alkylsulfinyl, $C_{1-3}$ alkylsulfonyl, $C_{1-3}$ alkylcarbonyl, $C_{1-3}$ alkoxycarbonyl, aminocarbonyl, $C_{1-3}$ alkylaminocarbonyl, N,N-di-($C_{1-3}$ alkyl)aminocarbonyl, amino, $C_{1-3}$ alkylamino, formylamino, $C_{1-3}$ alkylcarbonylamino, $C_{1-3}$ haloalkylcarbonylamino, and $C_{1-3}$ alkylsulfonylamino.

In further preferred embodiments $R^1$ is $C_{3-6}$ cycloalkyl optionally substituted with halogen, $C_{1-3}$ alkyl, $C_{1-3}$ haloalkyl, or $C_{1-3}$ alkoxy; $C_{3-6}$ cycloalkenyl optionally substituted with halogen, $C_{1-3}$ alkyl, $C_{1-3}$ haloalkyl, or $C_{1-3}$ alkoxy; $C_{2-6}$ alkynyl optionally substituted with halogen, hydroxyl, cyano, $C_{1-3}$ alkoxy, $C_{1-3}$ haloalkoxy, or $C_{1-3}$ alkylthio.

In particularly preferred embodiments, $R^1$ is $C_{1-3}$ alkyl substituted with halogen, cyano, cyclopropyl, $C_{1-3}$ alkoxy, allyloxy, propargyloxy, $C_{1-3}$ alkylthio, $C_{1-3}$ alkylsulfinyl, $C_{1-3}$ alkylsulfonyl, formyl, $C_{1-3}$ alkylcarbonyl, cyclopropylcarbonyl, $C_{1-3}$ haloalkylcarbonyl, $C_{1-3}$ alkoxycarbonyl, $C_{1-3}$ alkylthiocarbonyl, aminocarbonyl, $C_{1-3}$alkylaminocarbonyl, N,N-di-($C_{1-3}$ alkyl)aminocarbonyl, $C_{1-3}$ alkylcarbonyloxy, $C_{1-3}$ haloalkylcarbonyloxy, cyclopropylcarbonyloxy, benzoyloxy, or $C_{1-3}$ alkoxycarbonyloxy; or $C_{2-4}$ alkenyl, optionally substituted with halogen, cyano, $C_{1-3}$ alkoxy, $C_{1-3}$ haloalkoxy, $C_{1-3}$ alkylthio, $C_{1-3}$ haloalkylthio, $C_{1-3}$ alkylsulfinyl, $C_{1-3}$ alkylsulfonyl, $C_{1-3}$ alkylcarbonyl, or $C_{1-3}$ alkoxycarbonyl; or $C_{2-4}$ alkynyl optionally substituted with halogen, cyano, or $C_{1-3}$ alkoxy.

In the most preferred embodiments, $R^1$ is $C_{1-3}$ alkyl substituted with halogen, cyano, cyclopropyl, or $C_{1-2}$ alkoxy; or allyl, optionally substituted with halo, cyano, or $C_{1-2}$ alkoxy; or propargyl, optionally substituted with halogen, cyano, or $C_{1-2}$ alkoxy; or cyclopropyl, optionally substituted with halogen or $C_{1-2}$ alkyl.

In certain embodiments, including any of those described hereinbefore, Z is hydrogen, cyano, formyl, $C_{1-6}$ alkyl [optionally substituted by 1-7 fluorine atoms, 1-3 chlorine atoms, 1-3 bromine atoms, a cyano group, 1-2 $C_{1-3}$ alkoxy groups, a $C_{1-3}$ haloalkoxy group, a $C_{1-3}$ alkylthio group, a $C_{1-3}$ haloalkylthio group, an allyloxy group, a propargyloxy group, a $C_{3-6}$ cycloalkyl group, phenyl (itself optionally substituted by halogen, nitro, cyano, $C_{1-3}$ alkyl, $C_{1-3}$ alkoxy), a $C_{1-3}$ alkylcarbonyloxy group, a $C_{1-3}$ alkoxycarbonyl group, a $C_{1-3}$ alkylcarbonyl group, benzoyl (itself optionally substituted by halogen, nitro, $C_{1-3}$ alkyl, $C_{1-3}$ alkoxy, or a cyano group)], $C_{3-6}$ alkenyl, $C_{3-6}$ haloalkenyl, $C_{3-6}$ alkinyl, $C_{1-6}$ alkylthio, $C_{1-6}$ haloalkylthio, $C_{1-6}$ cyanoalkylthio, phenylthio (optionally substituted by halogen, nitro, cyano, $C_{1-3}$ alkyl, or $C_{1-3}$ alkoxy), $C_{1-6}$ alkyldithio, di($C_{1-4}$ alkyl)aminothio, $C_{1-6}$ alkylcarbonyl (optionally substituted by halogen, cyano, or $C_{1-3}$ alkoxy), $C_{2-6}$ alkenylcarbonyl, $C_{3-6}$ cycloalkylcarbonyl, phenylcarbonyl (optionally substituted by halogen, nitro, cyano, $C_{1-3}$ alkyl, or $C_{1-3}$ alkoxy), heteroarylcarbonyl (optionally substituted by halogen, nitro, cyano, $C_{1-3}$ alkyl, or $C_{1-3}$ alkoxy), $C_{1-6}$ alkoxycarbonyl, $C_{1-6}$ alkylthio-carbonyl, phenylthio-carbonyl (optionally substituted by halogen, nitro, cyano, $C_{1-3}$ alkyl, or $C_{1-3}$ alkoxy), N,N-di $C_{1-3}$ alkylaminocarbonyl, $C_{1-3}$ alkylaminocarbonyl, $C_{3-6}$ alkenylaminocarbonyl, $C_{3-6}$ alkynylaminocarbonyl, phenylaminocarbonyl (in which the phenyl group can be optionally substituted by halogen, nitro, cyano, $C_{1-3}$ alkyl, or $C_{1-3}$ alkoxy), N-phenyl-N-methyl aminocarbonyl (in which the phenyl group can be optionally substituted by halogen, nitro, cyano, $C_{1-3}$ alkyl, or $C_{1-3}$ alkoxy), $C_{1-6}$ alkoxythionocarbonyl, $C_{1-6}$ alkylthiothionocarbonyl, phenylthiothionocarbonyl (optionally substituted by halogen, nitro, cyano, $C_{1-3}$ alkyl, or $C_{1-3}$ alkoxy). N,N-di $C_{1-3}$ alkylaminothionocarbonyl, $C_{1-3}$ alkylaminothionocarbonyl, phenylaminothionocarbonyl (in which the phenyl group can be optionally substituted by halogen, nitro, cyano, $C_{1-3}$ alkyl, or $C_{1-3}$ alkoxy), N-phenyl-N-methyl aminothionocarbonyl (in which the phenyl group can be optionally substituted by halogen, nitro, cyano, $C_{1-3}$ alkyl, or $C_{1-3}$ alkoxy), $C_{1-3}$ alkylsulfonyl, $C_{1-3}$ haloalkylsulfonyl, $C_{1-3}$ alkenylsulfonyl, phenylsulfonyl (optionally substituted by halogen, nitro, cyano, $C_{1-3}$ alkyl, or $C_{1-3}$ alkoxy), N,N-di $C_{1-3}$ alkylaminosulfonyl, di $C_{1-3}$ alkoxy-P(=O)—, di $C_{1-3}$ alkylthio-P(=O)—, di $C_{1-3}$ alkoxy-P(=S)—, di $C_{1-3}$ alkylthio-P(=S)—, ($C_{1-3}$ alkoxy)(phenyl)(P=O)—, ($C_{1-3}$ alkoxy)(phenyl)(P=S)—, $C_{1-3}$ alkyl-N=CH—, $C_{1-3}$ alkoxy-N=CH—, cyano-N=CH—, phenyl-N=CH— (in which the phenyl is optionally substituted by halogen, nitro, cyano, $C_{1-3}$ alkyl, or $C_{1-3}$ alkoxy), 2-pyridyl-N=CH—, 3-pyridyl-N=CH—, 2-thiazolyl-N=CH—, or a compound of formula (II) wherein B is S—, or $CH_2$—.

More preferably Z is hydrogen, cyano, formyl, $C_{1-3}$ alkyl, $C_{1-3}$ haloalkyl, $C_{1-3}$ cyanoalkyl, $C_{1-3}$ alkoxy-$C_{1-3}$ alkyl, allyl, propargyl, $C_{1-6}$ alkylthio, $C_{1-6}$ haloalkylthio, phenylthio (optionally substituted by halogen, $C_{1-3}$ alkyl or $C_{1-3}$ alkoxy), $C_{1-6}$ alkylcarbonyl, phenylcarbonyl (optionally substituted by halogen, $C_{1-3}$ alkyl or $C_{1-3}$ alkoxy), $C_{1-6}$ alkoxycarbonyl, $C_{1-3}$ alkylaminocarbonyl, phenylaminocarbonyl (in which the phenyl group can be optionally substituted by halogen, $C_{1-3}$ alkyl or $C_{1-3}$ alkoxy), $C_{1-3}$ alkylaminothionocarbonyl, phenylaminothionocarbonyl (in which the phenyl group can be optionally substituted by halogen, $C_{1-3}$ alkyl or $C_{1-3}$ alkoxy), $C_{1-3}$ alkylsulfonyl, $C_{1-3}$ haloalkylsulfonyl, di($C_{1-3}$ alkoxy)-P(=O)—, $C_{1-3}$ alkoxy-N=CH—, cyano-N=CH—, 2-pyridyl-N=CH—. Most preferably Z is hydrogen.

In certain embodiments, including any of those described hereinbefore each $R^2$ and $R^3$ group is independantly methyl, halomethyl, or halogen, $R^4$ is hydrogen, and each $R^5$ and $R^6$ is independantly hydrogen or halogen. Preferably each $R^2$ and $R^3$ group is independantly methyl, fluoromethyl, difluoromethyl, trifluoromethyl, fluoro or chloro, and preferably each $R^5$ and $R^6$ is independently hydrogen or fluoro. Most preferably $R^5$ and $R^6$ are each hydrogen.

The compounds described below are illustrative of novel compounds of the invention. Table I provides 184 compounds of formula Ia:

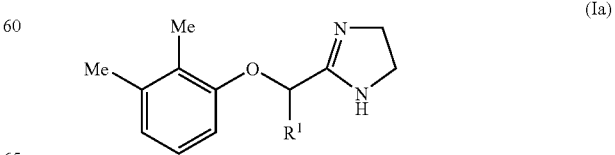

(Ia)

wherein the values of $R^1$ are given in Table 1.

TABLE 1

| Compound No | R¹ |
|---|---|
| I-1 | —CH=CH$_2$ |
| I-2 | —CF=CH$_2$ |
| I-3 | —CH=CHF |
| I-4 | —CH=CF$_2$ |
| I-5 | —CF=CF$_2$ |
| I-6 | —CCl=CH$_2$ |
| I-7 | —CH=CHCl |
| I-8 | —CH=CCl$_2$ |
| I-9 | —CCl=CCl$_2$ |
| I-10 | —CBr=CH$_2$ |
| I-11 | —CH=CHBr |
| I-12 | —CH=CBr$_2$ |
| I-13 | —CBr=CBr$_2$ |
| I-14 | —CH=CFCl |
| I-15 | —CH=CHOMe |
| I-16 | —C(OMe)=CH$_2$ |
| I-17 | —CH=CHSMe |
| I-18 | —C(SMe)=CH$_2$ |
| I-19 | —CMe=CH$_2$ |
| I-20 | —CH=CHMe |
| I-21 | —CH=CMe$_2$ |
| I-22 | —CMe=CMe$_2$ |
| I-23 | —CMe=CF$_2$ |
| I-24 | —CMe=CCl$_2$ |
| I-25 | —CMe=CHF |
| I-26 | —CMe=CHCl |
| I-27 | —CF=CHMe |
| I-28 | —CCl=CHMe |
| I-29 | —CH=CFMe |
| I-30 | —CH=CClMe |
| I-31 | —CH=CHCH$_2$OMe |
| I-32 | —CH=CHCH$_2$SMe |
| I-33 | —CH=CHCH$_2$OH |
| I-34 | —CH=CHCH$_2$F |
| I-35 | —CH=CHCF$_3$ |
| I-36 | —C(=CH$_2$)CH$_2$OH |
| I-37 | —C(=CH$_2$)CH$_2$OMe |
| I-38 | —C(=CH$_2$)CH$_2$SMe |
| I-39 | —C(=CH$_2$)CF$_3$ |
| I-40 | —CH=CHEt |
| I-41 | —CEt=CH$_2$ |
| I-42 | —CH=CHCH$_2$CH$_2$OH |
| I-43 | —CH=CHCH$_2$CH$_2$OMe |
| I-44 | —CH=CHCH$_2$CH$_2$SMe |
| I-45 | —CH=CHCH$_2$CH$_2$F |
| I-46 | —CH=CHCH$_2$CH$_2$Cl |
| I-47 | —CH=CHCH(Me)OMe |
| I-48 | —CH=CHCH(Me)F |
| I-49 | —CH=CHCHMeSMe |
| I-50 | —CH$_2$CH=CH$_2$ |
| I-51 | —CH$_2$CF=CH$_2$ |
| I-52 | —CH$_2$CH=CHF |
| I-53 | —CH$_2$CH=CF$_2$ |
| I-54 | —CH$_2$CF=CF$_2$ |
| I-55 | —CH$_2$CCl=CH$_2$ |
| I-56 | —CH$_2$CH=CHCl |
| I-57 | —CH$_2$CH=CCl$_2$ |
| I-58 | —CH$_2$CCl=CCl$_2$ |
| I-59 | —CH$_2$CBr=CH$_2$ |
| I-60 | —CH$_2$CH=CHBr |
| I-61 | —CH$_2$CH=CBr$_2$ |
| I-62 | —CH$_2$CBr=CBr$_2$ |
| I-63 | —CH$_2$CH=CFCl |
| I-64 | —CH$_2$CH=CHOMe |
| I-65 | —CH$_2$C(OMe)=CH$_2$ |
| I-66 | —CH$_2$CH=CHSMe |
| I-67 | —CH$_2$C(SMe)=CH$_2$ |
| I-68 | —CH$_2$CMe=CH$_2$ |
| I-69 | —CH(OH)CH=CH$_2$ |
| I-70 | —CHFCH=CH$_2$ |
| I-71 | —CH(OMe)CH=CH$_2$ |
| I-72 | —CH$_2$CH=CHMe |
| I-73 | —CH$_2$CH=CMe$_2$ |
| I-74 | —CH$_2$CMe=CMe$_2$ |
| I-75 | —CH$_2$CMe=CF$_2$ |
| I-76 | —CH$_2$CMe=CCl$_2$ |
| I-77 | —CH$_2$CMe=CHF |
| I-78 | —CH$_2$CMe=CHCl |
| I-79 | —CH$_2$CF=CHMe |
| I-80 | —CH$_2$CCl=CHMe |
| I-81 | —CH$_2$CH=CFMe |
| I-82 | —CH$_2$CH=CClMe |
| I-83 | —CH$_2$CH=CHCH$_2$OMe |
| I-84 | —CH$_2$CH=CHCH$_2$SMe |
| I-85 | —CH$_2$CH=CHCH$_2$OH |
| I-86 | —CH$_2$CH=CHCH$_2$F |
| I-87 | —CH$_2$CH=CHCF$_3$ |
| I-88 | —CH$_2$C(=CH$_2$)CH$_2$OH |
| I-89 | —CH$_2$C(=CH$_2$)CH$_2$OMe |
| I-90 | —CH$_2$C(=CH$_2$)CH$_2$SMe |
| I-91 | —CH$_2$C(=CH$_2$)CF$_3$ |
| I-92 | —C≡CH |
| I-93 | —C≡CMe |
| I-94 | —C≡CCH$_2$OH |
| I-95 | —C≡CCH$_2$F |
| I-96 | —C≡CCH$_2$OMe |
| I-97 | —C≡CCH$_2$SMe |
| I-98 | —C≡CEt |
| I-99 | —C≡CCH$_2$CH$_2$OH |
| I-100 | —C≡CCH$_2$CH$_2$F |
| I-101 | —C≡CCH$_2$CH$_2$OMe |
| I-102 | —C≡CCH$_2$CH$_2$SMe |
| I-103 | —C≡CCHMeOH |
| I-104 | —C≡CCHMeOMe |
| I-105 | —C≡CHMeSMe |
| I-106 | —CH$_2$C≡CH |
| I-107 | —CH$_2$C≡CMe |
| I-108 | —CH$_2$C≡CCH$_2$OH |
| I-109 | —CH$_2$C≡CCH$_2$F |
| I-110 | —CH$_2$C≡CCH$_2$OMe |
| I-111 | —CH$_2$C≡CCH$_2$SMe |
| I-112 | —CH(OH)C≡CH |
| I-113 | —CHFC≡CH |
| I-114 | —CH(OMe)C≡CH |
| I-115 | —CH(SMe)C≡CH |
| I-116 | —CH$_2$CH$_2$C≡CH |
| I-117 | —CH$_2$CH$_2$C≡CMe |
| I-118 | —CH$_2$OH |
| I-119 | —CH$_2$F |
| I-120 | —CH$_2$Cl |
| I-121 | —CH$_2$OMe |
| I-122 | —CH$_2$SMe |
| I-123 | —CH$_2$S(O)Me |
| I-124 | —CH$_2$S(O)$_2$Me |
| I-125 | —CH$_2$NMe$_2$ |
| I-126 | —CH$_2$CH$_2$OH |
| I-127 | —CH$_2$CH$_2$F |
| I-128 | —CH$_2$CH$_2$Cl |
| I-129 | —CH$_2$CH$_2$OMe |
| I-130 | —CH$_2$CH$_2$SMe |
| I-131 | —CH$_2$CH$_2$S(O)Me |
| I-132 | —CH$_2$CH$_2$S(O)$_2$Me |
| I-133 | —CH(OH)Me |
| I-134 | —CHFMe |
| I-135 | —CH(OMe)Me |
| I-136 | —CH(SMe)Me |
| I-137 | —CH$_2$CH$_2$CH$_2$OH |
| I-138 | —CH$_2$CH$_2$CH$_2$F |
| I-139 | —CH$_2$CH$_2$CH$_2$Cl |
| I-140 | —CH$_2$CH$_2$CH$_2$OMe |
| I-141 | —CH$_2$CH$_2$CH$_2$SMe |
| I-142 | —CH$_2$CH$_2$CH$_2$S(O)Me |
| I-143 | —CH$_2$CH$_2$CH$_2$S(O)$_2$Me |
| I-144 | —CH$_2$CH$_2$CH$_2$NMe$_2$ |
| I-145 | —CHMeCH$_2$OH |
| I-146 | —CHMeCH$_2$F |
| I-147 | —CHMeCH$_2$Cl |
| I-148 | —CHMeCH$_2$OMe |
| I-149 | —CHMeCH$_2$SMe |
| I-150 | —CHMeCH$_2$S(O)Me |

TABLE 1-continued

R[1]

| Compound No | R[1] |
|---|---|
| I-151 | —CHMeCH$_2$S(O)$_2$Me |
| I-152 | —CHMeCH$_2$NMe$_2$ |
| I-153 | —CH$_2$CHMeOH |
| I-154 | —CH$_2$CHMeF |
| I-155 | —CH$_2$CHMeCl |
| I-156 | —CH$_2$CHMeOMe |
| I-157 | —CH$_2$CHMeSMe |
| I-158 | —CH$_2$CHMeS(O)Me |
| I-159 | —CH$_2$CHMeS(O)$_2$Me |
| I-160 | —CH(OH)Et |
| I-161 | —CHFEt |
| I-162 | —CH(OMe)Et |
| I-163 | —CH(SMe)Et |
| I-164 | cyclopropyl |
| I-165 | cyclobutyl |
| I-166 | cyclopentyl |
| I-167 | cyclohexyl |
| I-168 | 1-methylcyclopropyl |
| I-169 | 2-methylcyclopropyl |
| I-170 | 1-methylcyclopentyl |
| I-171 | cyclopropylmethyl |
| I-172 | cyclobutylmethyl |
| I-173 | phenyl |
| I-174 | 4-fluorophenyl |
| I-175 | 4-Chlorophenyl |
| I-176 | 4-methoxyphenyl |
| I-177 | 2-pyridyl |
| I-178 | 4-pyridyl |
| I-179 | cyclopropylethyl |
| I-180 | cyclobutylethyl |
| I-181 | —CH$_2$Ph |
| I-182 | —CH$_2$-(4-fluorophenyl) |
| I-183 | —CH$_2$-(2-pyridyl) |
| I-184 | —CH$_2$-(4-pyridyl) |

184 Compounds of formula Ib

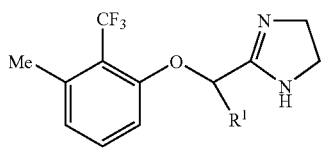

(Ib)

wherein the values of R[1] are as given in Table 1 for compounds I-1 to I-184, are designated as compound Nos. II-1 to II-184, respectively.

184 Compounds of formula Ic

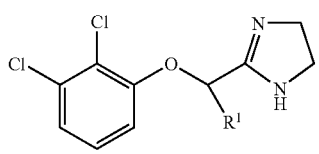

(Ic)

wherein the values of R1 are as given in Table 1 for compounds I-1 to I-184, are designated as compound Nos. III-1 to III-184, respectively 184 Compounds of formula Id

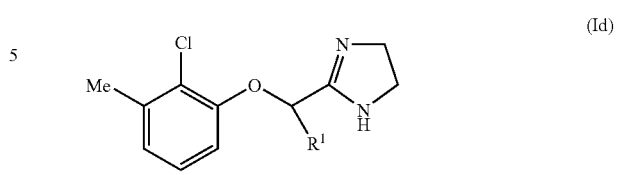

(Id)

wherein the values of R1 are as given in Table 1 for compounds I-1 to I-184, are designated as compound Nos. IV-1 to IV-184, respectively.

184 Compounds of formula Ie

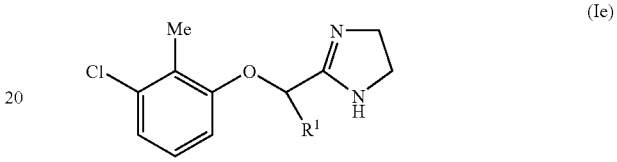

(Ie)

wherein the values of R[1] are as given in Table 1 for compounds I-1 to I-184, are designated as compound Nos. V-1 to V-184, respectively.

184 Compounds of formula If

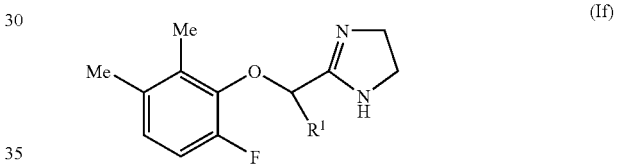

(If)

wherein the values of R1 are as given in Table 1 for compounds I-1 to I-184, are designated as compound Nos. VI-1 to VI-184, respectively.

184 Compounds of formula Ig

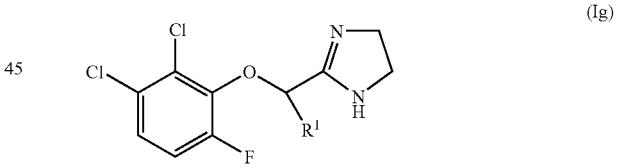

(Ig)

wherein the values of R1 are as given in Table 1 for compounds I-1 to I-184, are designated as compound Nos. VII-1 to VII-184, respectively.

184 compounds of formula Ih

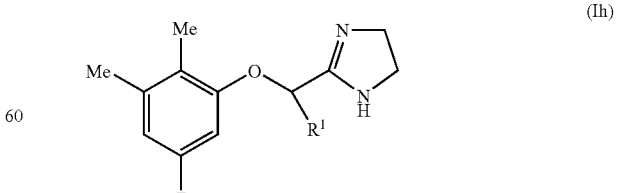

(Ih)

wherein the values of R1 are as given in Table 1 for compounds I-1 to I-184, are designated as compound Nos. VIII-1 to VIII-184, respectively.

184 Compounds of formula Ij

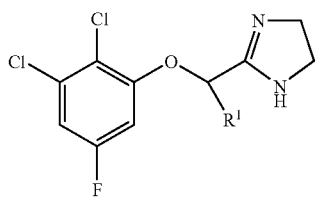
(Ij)

wherein the values of R¹ are as given in Table 1 for compounds I-1 to I-184, are designated as compound Nos. IX-1 to IX-184, respectively.

184 compounds of formula Iaa

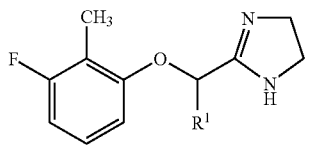
(Iaa)

wherein the values of R¹ are as given in Table 1 for compounds I-1 to I-184, are designated as compound Nos. XXXI-1 to XXXI-184, respectively.

184 compounds of formula Iab

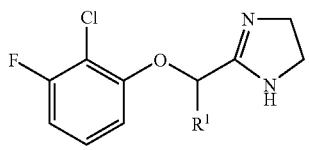
(Iab)

wherein the values of R¹ are as given in Table 1 for compounds I-1 to I-184, are designated as compound Nos. XXXII-1 to XXXII-184, respectively.

184 compounds of formula Iac

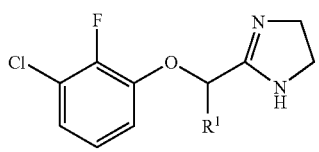
(Iac)

wherein the values of R¹ are as given in Table 1 for compounds I-1 to I-184, are designated as compound Nos. XXXIII-1 to XXXIII-184, respectively.

184 compounds of formula Iad

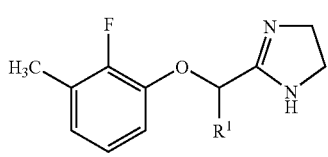
(Iad)

wherein the values of R¹ are as given in Table 1 for compounds I-1 to I-184, are designated as compound Nos. XXXIV-1 to XXXIV-184, respectively.

184 compounds of form Iae

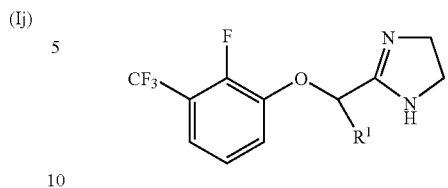
(Iae)

wherein the values of R¹ are as given in Table 1 for compounds I-1 to I-184, are designated as compound Nos. XXXV-1 to XXXV-184, respectively.

184 compounds of formula Iaf

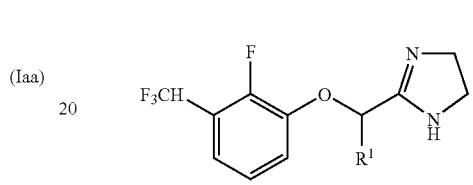
(Iaf)

wherein the values of R¹ are as given in I able 1 for compounds I-1 to I-184, are designated as compound Nos. XXXVI-1 to XXXVI-184, respectively.

184 compounds of formula Iag

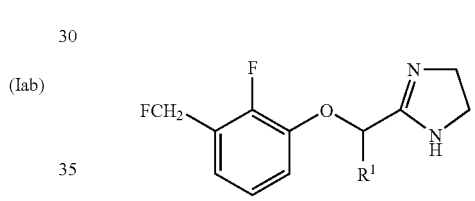
(Iag)

wherein the values of R¹ are as given in Table 1 for compounds I-1 to I-184, are designated as compound Nos. XXXVII-1 to XXXVII-184, respectively.

Table XXXVII provides 184 compounds of formula Iah

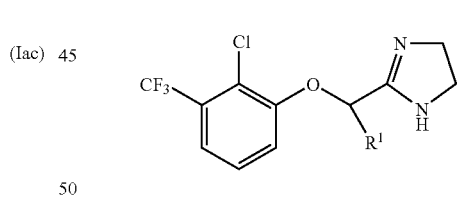
(Iah)

wherein the values of R¹ are as given in Table 1 for compounds I-1 to I-184, are designated as compound Nos. XXXVIII-1 to XXXVIII-184, respectively.

184 compounds of formula Iai

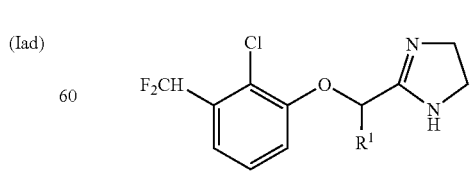
(Iai)

wherein the values of R¹ are as given in Table 1 for compounds I-1 to I-184, are designated as compound Nos. XXXIX-1 to XXXIX-184, respectively.

184 compounds of formula Iaj

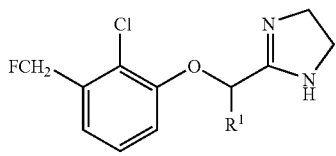
(Iaj)

wherein the values of R¹ are as given in Table 1 for compounds I-1 to I-184, are designated as compound Nos. XL-1 to XL-184, respectively.

184 compounds of formula Iak

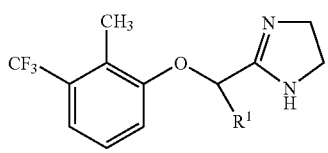
(Iak)

wherein the values of R¹ are as given in Table 1 for compounds I-1 to I-184, are designated as compound Nos. XLI-1 to LI-184, respectively.

184 compounds of formula Ial

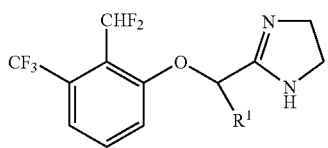
(Ial)

wherein the values of R¹ are as given in Table 1 for compounds I-1 to I-184, are designated as compound Nos. XLII-1 to XLII-184, respectively.

184 compounds of formula Iam

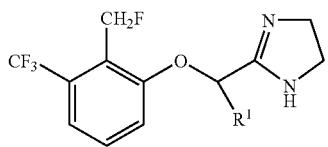
(Iam)

wherein the values of R¹ are as given in Table 1 for compounds I-1 to I-184, are designated as compound Nos. XLIII-1 to XLIII-184, respectively.

184 compounds of formula Ian

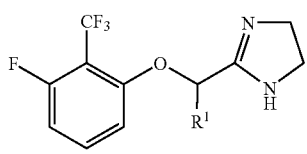
(Ian)

wherein the values of R¹ are as given in Table 1 for compounds I-1 to I-184, are designated as compound Nos. XLIV-1 to XLIV-184, respectively.

184 compounds of formula Iao

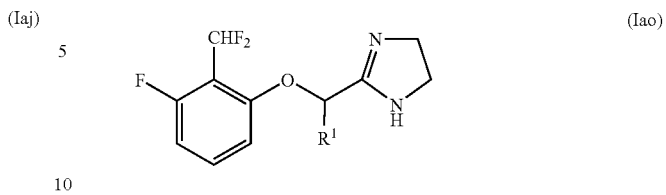
(Iao)

wherein the values of R¹ are as given in Table 1 for compounds I-1 to I-184, are designated as compound Nos. XLV-1 to XV-184 respectively.

184 compounds formula Iap

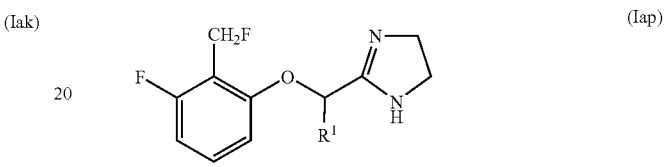
(Iap)

wherein the values of R¹ are as given in Table 1 for compounds I-1 to I-184, are designated as compound Nos. XLVI-1 to XLVI-184, respectively.

184 compounds of formula Iaq

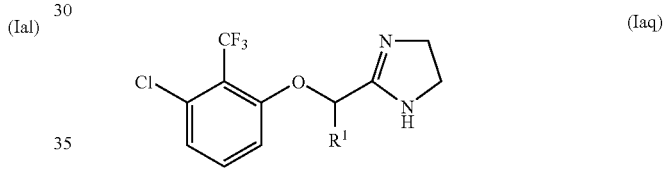
(Iaq)

wherein the values of R¹ are as given in Table 1 for compounds I-1 to I-184, are designated as compound Nos. XLVII-1 to XLVII-184, respectively.

184 compounds of formula Iar

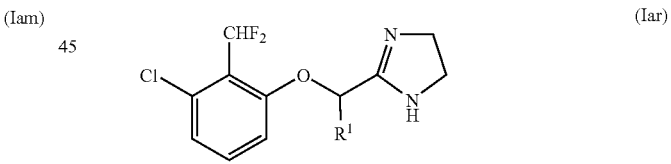
(Iar)

wherein the values of R¹ are as given in Table 1 for compounds I-1 to I-184, are designated as compound Nos. XLVIII-1 to XLVIII-184, respectively.

184 compounds of formula Ias

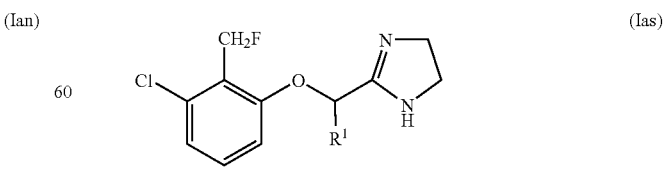
(Ias)

wherein the values of R¹ are as given in Table 1 for compounds I-1 to I-184, are designated as compound Nos. XLIX-1 to XLIX-184, respectively.

Table 2 provides 96 compounds of formula Ik

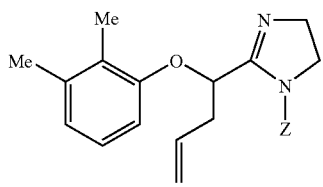

wherein the values of Z are as given in Table 2 below.

TABLE 2

Z substitutions

| Compound No | Z |
|---|---|
| X-1 | —CN |
| X-2 | —NO$_2$ |
| X-3 | Me |
| X-4 | Et |
| X-5 | Pr |
| X-6 | Bu |
| X-7 | allyl |
| X-8 | isopropenyl |
| X-9 | vinyl |
| X-10 | but-2-en1-yl |
| X-11 | but-1-en-1-yl |
| X-12 | but-3-en1-yl |
| X-13 | but-1-en2-yl |
| X-14 | but-2-en2-yl |
| X-15 | but-3-en2-yl |
| X-16 | methoxymethyl |
| X-17 | ethoxymethyl |
| X-18 | propoxymethyl |
| X-19 | benzyloxymethyl |
| X-20 | 1-methoxyethyl |
| X-21 | 2-methoxyethyl |
| X-22 | —CH$_2$OCOMe |
| X-23 | —CH$_2$OCOEt |
| X-24 | —CH$_2$OCOiPr |
| X-25 | —CH$_2$OCOtBu |
| X-26 | —CH$_2$OCOPh |
| X-27 | —CH$_2$OCOEt |
| X-28 | —CH=N—OMe |
| X-29 | —CH=N—OEt |
| X-30 | —CH=N-Me |
| X-31 | —CH=N-Et |
| X-32 | —CH=N-Ph |
| X-33 | —CH=N-2-pyridyl |
| X-34 | —CH=N—C=N |
| X-35 | —P(O)(OEt)$_2$ |
| X-36 | —P(S)(OEt)$_2$ |
| X-37 | —P(O)(OMe)$_2$ |
| X-38 | —P(S)(OMe)$_2$ |
| X-39 | —P(O)(OPh)$_2$ |
| X-40 | —P(S)(OPh)$_2$ |
| X-41 | —P(O)(OBn)$_2$ |
| X-42 | —P(S)(OBn)$_2$ |
| X-43 | —P(O)(NMe$_2$)$_2$ |
| X-44 | —P(S)(NMe$_2$)$_2$ |
| X-45 | —P(O)(NEt$_2$)$_2$ |
| X-46 | —P(S)(NEt$_2$)$_2$ |
| X-47 | —OH |
| X-48 | —OMe |
| X-49 | —OAc |
| X-50 | —OBz |
| X-51 | SMe |
| X-52 | SCCl$_3$ |
| X-53 | SPh |
| X-54 | S(O)Ph |
| X-55 | S(O)$_2$Me |
| X-56 | S(O)$_2$CF$_3$ |
| X-57 | S(O)$_2$Ph |
| X-58 | C(O)Me |

TABLE 2-continued

Z substitutions

| Compound No | Z |
|---|---|
| X-59 | C(O)Et |
| X-60 | C(O)iPr |
| X-61 | C(O)tBu |
| X-62 | C(O)CH$_2$OMe |
| X-63 | C(O)CH$_2$Cl |
| X-64 | C(O)CHCl$_2$ |
| X-65 | C(O)CCl$_3$ |
| X-66 | C(O)Ph |
| X-67 | C(O)(4-fluorophenyl) |
| X-68 | C(O)(4-chlorophenyl) |
| X-69 | C(O)(4-methoxyphenyl) |
| X-70 | C(O)(2,4-dichlorophenyl) |
| X-71 | C(O)(2,6-dichlorophenyl) |
| X-72 | C(O)(2,6-difluorophenyl) |
| X-73 | C(O)OMe |
| X-74 | C(O)OEt |
| X-75 | C(O)OiPr |
| X-76 | C(O)OtBu |
| X-77 | C(O)OPh |
| X-78 | C(O)O(4-fluorophenyl) |
| X-79 | C(O)O(4-chlorophenyl) |
| X-80 | C(O)O(4-methoxyphenyl) |
| X-81 | C(O)O(2,4-dichlorophenyl) |
| X-82 | C(O)O(2,6-dichlorophenyl) |
| X-83 | C(O)O(2,6-difluorophenyl) |
| X-84 | C(O)NHMe |
| X-85 | C(O)NMe$_2$ |
| X-86 | C(O)NHEt |
| X-87 | C(O)NEt$_2$ |
| X-88 | C(O)NHiPr |
| X-89 | C(O)NHtBu |
| X-90 | C(O)NHPh |
| X-91 | C(O)NH(4-fluorophenyl) |
| X-92 | C(O)NH(4-chlorophenyl) |
| X-93 | C(O)NH(4-methoxyphenyl) |
| X-94 | C(O)NH(2,4-dichlorophenyl) |
| X-95 | C(O)NH(2,6-dichlorophenyl) |
| X-96 | C(O)NH(2,6-difluorophenyl) |

96 Compounds of formula II

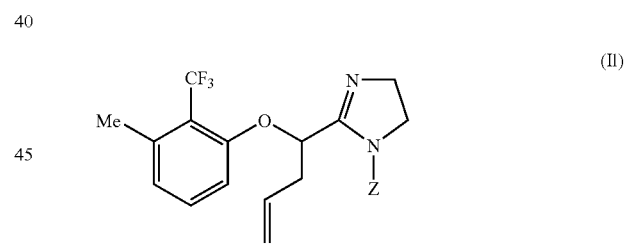

wherein the values of Z are as given in Table 2 for compounds X-1 to X-96, are designated as compound Nos. XI-1 to XI-96, respectively.

96 Compounds of formula Im

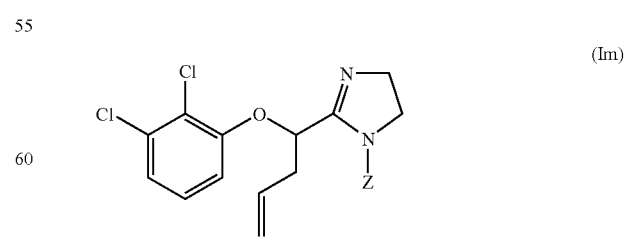

wherein the values of Z are as given in Table 2 for compounds X-1 to X-96, are designated as compound Nos. XII-1 to XII-96, respectively.

96 Compounds of formula In

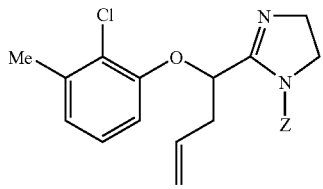

(In)

wherein the values of Z are as given in Table 2 for compounds X-1 to X-96, are designated as compound Nos. XIII-1 to XIII-96, respectively.

96 Compounds of formula Io

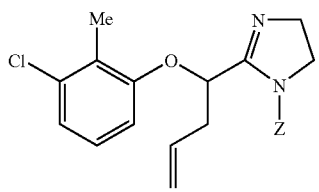

(Io)

wherein the values of Z are as given in Table 2 for compounds X-1 to X-96, are designated as compound Nos. XIV-1 to XIV-96, respectively.

96 Compounds of formula Ip

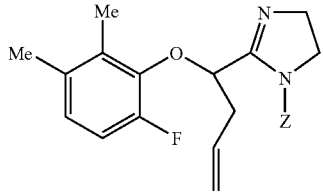

(Ip)

wherein the values of Z are as given in Table 2 for compounds X-1 to X-96, are designated as compound Nos. XV-1 to XV-96, respectively.

96 Compounds of formula Iq

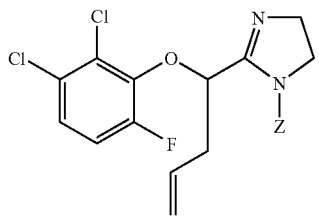

(Iq)

wherein the values of Z are as given in Table 2 for compounds X-1 to X-96, are designated as compound Nos. XVI-1 to XVI-96, respectively.

96 Compounds of formula Ir

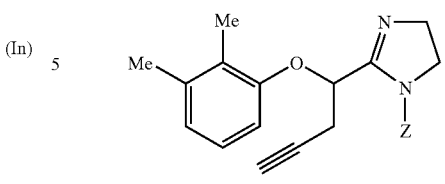

(Ir)

wherein the values of Z are as given in Table 2 for compounds X-1 to X-96, are designated as compound Nos. XVII-1 to XVII-96, respectively.

96 Compounds of formula Is

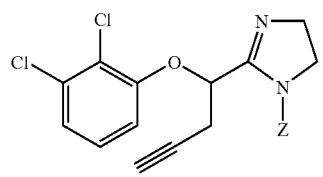

(Is)

wherein the values of Z are as given in Table 2 for compounds X-1 to X-96, are designated as compound Nos. XIX-1 to XIX-96, respectively.

96 Compounds of formula It

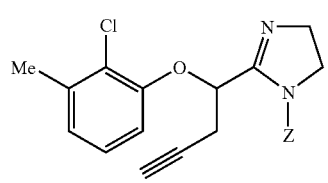

(It)

wherein the values of Z are as given in Table 2 for compounds X-1 to X-96, are designated as compound Nos. XX-1 to XX-96, respectively.

96 Compounds of formula Iu

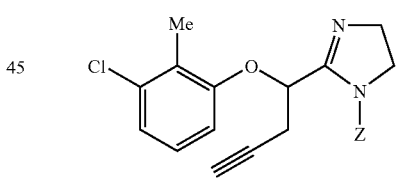

(Iu)

wherein the values of Z are as given in Table 2 for compounds X-1 to X-96, are designated as compound Nos. XXI-1 to XXI-96, respectively.

96 Compounds of formula Iv

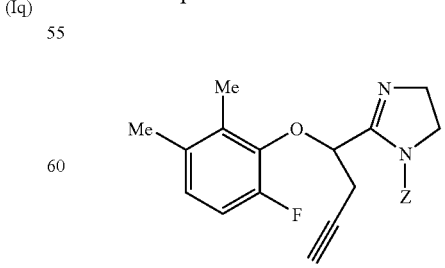

(Iv)

wherein the values of Z are as given in Table 2 for compounds X-1 to X-96, are designated as compound Nos. XXII-1 to XXII-96, respectively.

96 Compounds of formula Iw

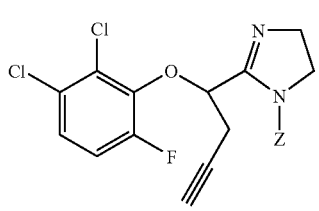
(Iw)

wherein the values of Z are as given in Table 2 for compounds X-1 to X-96, are designated as compound Nos. XXIII-1 to XXIII-96, respectively.

96 compounds of formula Iat

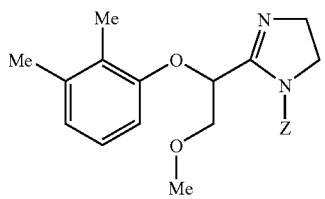
(Iat)

wherein the values of Z are as given in Table 2 for compounds X-1 to X-96, are designated as compound Nos. XXIV-1 to XXIV-96, respectively.

96 compounds of formula Iau

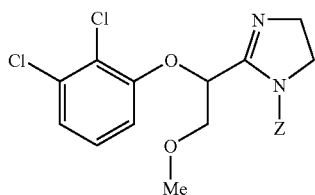
(Iau)

wherein the values of Z are as given in Table 2 for compounds X-1 to X-96, are designated as compound Nos. XXV-1 to XXV-96, respectively 96 compounds of formula Iav

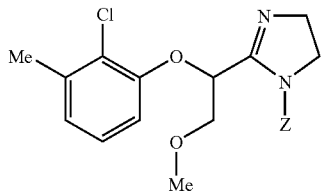
(Iav)

wherein the values of Z are as given in Table 2 for compounds X-1 to X-96, are designated as compound Nos. XXVI-1 to XXVI-96, respectively 96 compounds of formula Iaw

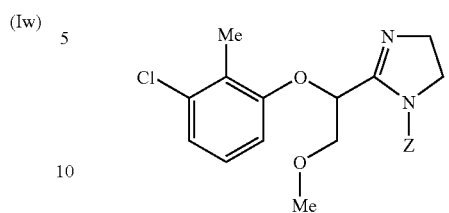
(Iaw)

wherein the values of Z are as given in Table 2 for compounds X-1 to X-96, are designated as compound Nos. XXVII-1 to XXVII-96, respectively 96 compounds of fnrmillA Iax

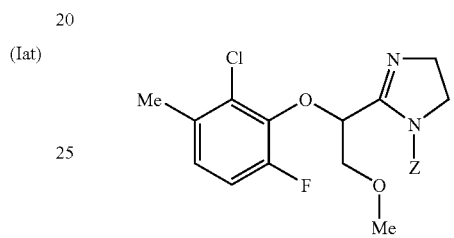
(Iax)

wherein the values of Z are as given in Table 2 for compounds X-1 to X-96, are designated as compound Nos. XXVIII-1 to XXVIII-96, respectively 96 compounds of formula Iay

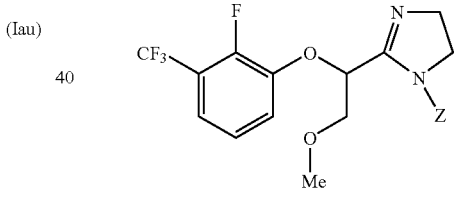
(Iay)

wherein the values of Z are as given in Table 2 for compounds X-1 to X-96, are designated as compound Nos. XXIX-1 to XXIX-96, respectively 96 compounds of formula m/z

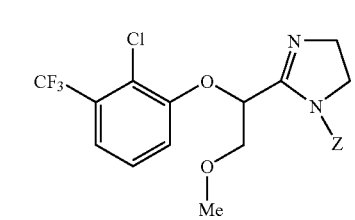
(Iaz)

wherein the values of Z are as given in Table 2 for compounds X-1 to X-96, are designated as compound Nos. XXX-1 to XXX-96, respectively Table 3 below provides characterising data for some of the compounds described above; other compounds are only described in this table of characterising data.

TABLE 3

Characterising data for compounds of the Invention.

| compound number | R¹ | R² | R³ | R⁴ | R⁵ | R⁶ | Z | m.p. [° C.] |
|---|---|---|---|---|---|---|---|---|
| I-50 | allyl | Me | Me | H | H | H | H | 72-74 |
| I-106 | propargyl | Me | Me | H | H | H | H | 70-73 |
| I-126 | FCH$_2$CH$_2$ | Me | Me | H | H | H | H | 107-109 |
| X-76 | allyl | Me | Me | H | H | H | tBuOCO | oil* |
| XVII-76 | propargyl | Me | Me | H | H | H | tBuOCO | oil* |
| 1.006 | FCH$_2$CH$_2$ | Me | Me | H | H | H | tBuOCO | oil* |
| 1.007 | CF$_3$CH(OH)— | Me | Me | H | H | H | H | 141-144 |
| III-50 | allyl | Cl | Cl | H | H | H | H | 125-131 |
| III-106 | propargyl | Cl | Cl | H | H | H | H | 125-131 |
| 1.010 | PhCH$_2$OCH$_2$ | Me | Me | H | H | H | H | oil* |
| 1.011 | CF$_3$CH(OH)— | Me | Me | H | H | H | tBuOCO | 118-123 |
| 1.012 | cyclohexyl | Me | Me | H | H | H | H | 131-133 |
| 1.013 | MeOCH$_2$ | Me | Me | H | H | H | H | 63-66 |
| 1.014 | Me(OH)CH | Me | Me | H | H | H | H | 124-128 |
| 1.015 | PhCH$_2$ | Me | Me | H | H | H | H | 113-116 |
| 1.016 | HOCH$_2$ | Me | Me | H | H | H | H | 142-145 |
| 1.017 | MeSCH$_2$ | Me | Me | H | H | H | H | 85-91 |
| 1.018 | H$_2$C=CClCH$_2$ | Me | Me | H | H | H | H | 73-77 |
| 1.019 | ClHC=CHCH$_2$[a] | Me | Me | H | H | H | H | 72-75 |
| 1.020 | Cl$_2$C=CHCH$_2$ | Me | Me | H | H | H | H | 121-125 |
| 1.021 | Me$_2$C=CHCH$_2$ | Me | Me | H | H | H | H | 99-102 |
| 1.022 | Me$_2$(HO)CCH$_2$ | Me | Me | H | H | H | H | * |
| 1.023 | hex-2-en-1-yl[c] | Me | Me | H | H | H | H | 120-123 |
| 1.024 | hex-2-en-1-yl[d] | Me | Me | H | H | H | H | 110-113 |
| 1.025 | H$_2$C=CHCHMe[c] | Me | Me | H | H | H | H | 89-91 |
| 1.026 | ClHC=CHCH$_2$[b] | Me | Me | H | H | H | H | * |
| 1.027 | Me$_2$(OH)CH$_2$CH$_2$ | Me | Me | H | H | H | H | 122-124 |
| 1.028 | [1,2,4]triazol-1-ylmethyl | Me | Me | H | H | H | H | 146-149 |
| 1.029 | H$_2$C=CMeCH$_2$ | Me | Me | H | H | H | H | 90-92 |
| 1.030 | H$_2$C=CHCHMe[d] | Me | Me | H | H | H | H | 75-78 |
| 1.031 | MeHC=CHCH$_2$[a] | Me | Me | H | H | H | H | 75-79 |
| 1.032 | MeHC=CHCH$_2$[b] | Me | Me | H | H | H | H | 80-103 |
| 1.033 | cPrCH$_2$ | Me | Me | H | H | H | H | * |
| 1.034 | EtOCH$_2$ | Me | Me | H | H | H | H | * |
| 1.035 | allyloxymethyl | Me | Me | H | H | H | H | * |
| 1.036 | 3-fluoropropyl | Me | Me | H | H | H | H | 75-78 |
| 1.037 | H$_2$C=CClCH$_2$ | Me | Me | H | H | H | H | 132-146 |
| 1.038 | cyclopropyl | Me | Me | H | H | H | H | 106-107.5 |
| 1.039 | cyclobutyl | Me | Me | H | H | H | H | 128-129 |
| 1.040 | MeNHC(S)— | Me | Me | H | H | H | H | |
| 1.041 | Allyl | F | F | H | F | H | H | 110-112 |
| 1.042 | Allyl | F | H | H | H | F | H | Gum* |
| 1.043 | Allyl | F | F | H | F | F | H | 86-88 |
| 1.044 | allyl | Me | F | H | F | H | H | 88-89 |
| 1.045 | allyl | Me | F | H | H | F | H | Gum* |
| 1.046 | allyl | Me | Cl | H | H | H | H | 122-123 |
| 1.047 | allyl | Cl | Me | H | H | H | H | Gum* |
| 1.048 | MeOCH$_2$— | Me | Cl | H | H | H | H | Gum* |
| 1.049 | MeOCH$_2$— | Cl | Cl | H | H | H | H | Solid* |
| 1.050 | MeOCH$_2$— | F | H | H | H | F | H | Gum* |
| 1.051 | MeOCH$_2$— | F | F | H | F | F | H | Gel* |
| 1.052 | MeOCH$_2$— | F | Me | H | H | F | H | Gel* |
| 1.053 | EtOCH$_2$— | Me | Cl | H | H | H | H | 115-116 |
| 1.054 | EtOCH$_2$— | Cl | Cl | H | H | H | H | 124-125 |
| 1.055 | EtOCH$_2$— | F | H | H | H | F | H | Gel* |
| 1.056 | EtOCH$_2$— | F | F | H | F | F | H | Gel* |
| 1.057 | EtOCH$_2$— | F | Me | H | H | F | H | Gel* |
| 1.058 | EtOCH$_2$— | Cl | Me | H | H | H | H | 105-107 |
| 1.059 | MeOCH$_2$— | Cl | Me | H | H | H | H | Solid* |
| 1.060 | MeOCH$_2$— | Cl | Me | H | H | F | H | Gum* |
| 1.061 | MeOCH$_2$— | F | Me | H | H | Cl | H | Gum* |
| 1.062 | MeOCH$_2$— | Cl | Me | H | F | H | H | Solid* |
| 1.063 | MeOCH$_2$— | Br | Me | H | H | H | H | Gum* |
| 1.064 | MeOCH$_2$— | I | Me | H | H | H | H | Gum* |
| 1.065 | allyl | Br | Me | H | H | H | H | Solid* |
| 1.066 | MeOCH$_2$— | F | CF$_3$ | H | H | H | H | Gum* |
| 1.067 | MeOCH$_2$CH$_2$OCH$_2$— | Cl | Me | H | H | H | H | Gum* |
| 1.068 | MeOCH$_2$ | Me | Me | H | H | H | H | 190-200 |
| 1.069 | MeOCHMe[c] | Me | Me | H | H | H | H | * |
| 1.070 | MeOCHMe[d] | Me | Me | H | H | H | H | * |
| 1.071 | MeC=CCH$_2$ | Me | Me | H | H | H | H | 112-116 |
| 1.072 | HOOCCH$_2$[e] | Me | Me | H | H | H | H | 136-140 |
| 1.073 | allyl | Me | Me | H | H | H | SO$_2$CH$_2$CMe=CH$_2$ | * |
| 1.074 | allyl | Me | Me | H | H | H | CH$_2$SMe | * |

TABLE 3-continued

Characterising data for compounds of the Invention.

| compound number | R¹ | R² | R³ | R⁴ | R⁵ | R⁶ | Z | m.p. [° C.] |
|---|---|---|---|---|---|---|---|---|
| 1.075 | allyl | Me | Me | H | H | H | MeOCH$_2$ | * |
| 1.076 | allyl | Me | Me | H | H | H | allylOCH$_2$ | * |
| 1.077 | allyl | Me | Me | H | H | H | CN | * |
| 1.078 | allyl | Me | Me | H | H | H | SO2Ph | * |
| 1.079 | MeSO$_2$OCH$_2$ | Me | Me | H | H | H | COOtBu | 88-95 |
| 1.080 | MeSO$_2$CH$_2$ | Me | Me | H | H | H | COOtBu | 113-116 |
| 1.081 | tBuOCOCH$_2$ | Me | Me | H | H | H | COOtBu | * |
| 1.082 | N≡CCH$_2$ | Me | Me | H | H | H | COOtBu | * |
| 1.083 | 3-chloropropyl | Me | Me | H | H | H | COOtBu | * |
| 1.084 | MeCOOCH$_2$ | Me | Me | H | H | H | COOtBu | * |
| 1.085 | N$_3$CH$_2$ | Me | Me | H | H | H | COOtBu | * |
| 1.086 | ClCH$_2$ | Me | Me | H | H | H | COOtBu | * |
| 1.087 | 1-tetrazolo methyl | Me | Me | H | H | H | COOtBu | * |
| 1.088 | H$_2$C═CH | Me | Me | H | H | H | COOtBu | * |
| 1.049 | MeOCH$_2$— | Cl | Me | H | H | H | H | 84-86 |

* = see NMR data below,
[a] = cis isomer,
[b] = trans isomer,
[c] = diastereomer A,
[d] = diastereomer B,
[e] = CF$_3$COOH salt ¹H-NMR (CDCl$_3$) of selected compounds:

X-76 6.97 dd 1H, 6.75 d 1H, 6.51 d 1H, 5.98 m 1H, 5.66 t 1H, 5.18 d 1H, 5.11 d 1H, 3.79 m 4H, 2.72 t 2H, 2.26 s 3H, 2.23 s 3H

XVII-76 7.00 dd 1H, 6.78 d 1H, 6.62 d 1H, 5.77 t 1H, 3.83 m 4H, 2.91 m 2H, 2.25 s 3H, 2.22 s 3H, 1.52 s 9H 1.006 6.99 dd 1H, 6.76 d 1H, 6.53 d 1H, 5.77 m 1H, 4.83-4.60 m 2H, 3.77 m 4H, 2.50-2.27 m 2H, 2.25 s 3H, 2.18 s 3H, 1.52 s 9H 1.010 7.31 m 5H, 7.01 dd 1H, 6.79 d 2H, 5.04 t 1H, 4.63 s 2H, 3.94 m 2H, 3.63 br s 4H, 2.29 s 3H, 2.02 s 3H 1.022 7.05 dd 1H, 6.81 d 1H, 6.77 d 1H, 5.15 t 1H, 4.42 br s 2H, 3.62 m 4H, 2.28 s 3H, 2.16 s 3H, 2.13 d 2H, 1.30 s 3H, 1.26 s 3H 1.026 7.03 dd 1H, 6.83 d 1H, 6.72 d 1H, 6.13 d 1H, 5.97 dt 1H, 5.14 dd 1H, 3.74 m 4H, 2.73 t 2H, 2.27 s 3H, 2.15 s 3H 1.033 7.01 dd 1H, 6.80 d 1H, 6.68 d 1H, 5.31 dd 1H, 3.80 m 4H, 2.25 s 3H, 2.16 s 3H, 2.02 m 1H, 1.78 m 1H, 0.89 m 1H, 0.47 m 2H, 0.13 br s 2H 1.034 7.00 dd 1H, 6.84 d 1H, 6.76 d 1H, 5.34 t 1H, 3.87 AB 2H, 3.80 m 4H, 3.55 q 2H; 2.25 s 3H; 2.16 s 3H, 1.16 t 3H 1.035 7.04 dd 1H, 6.85 d 1H, 6.76 d 1H, 5.87 m 1H, 5.40 br s 1H, 5.26 d 1H, 5.19 d 1H, 4.06 d 2H, 3.92 AB 2H, 3.82 m 4H, 2.27 s 3H, 2.16 s 3H 1.040 9.40 s 1H, 6.84 dd 1H, 6.88 d 1H, 6.55 d 1H, 6.02 br s 1H, 4.34 m 1H, 3.62 t 2H, 3.34 t 2H, 2.89 d 1H, 2.14 s 3H, 2.12 s 3H 1.042 6.98, m, 1H, 6.88, m, 1H, 6.88, t, 1H, 5.92, m, 1H, 5.20, dxd, 1H, 5.13, dxd, 1H, 4.88, t, 1H, 3.66, m, 2H, 3.52, m, 2H, 2.72, m, 2H.

1.045 6.86, m, 1H, 6.72, m, 1H, 5.96, m, 1H, 5.16, dxd, 1H, 5.10, dxd, 1H, 4.85, t, 1H, 3.68, m, 2H, 3.58, m, 2H, 2.70, m, 2H, 2.19, small d, 3H.

1.047 7.08, t, 1H, 6.88, d, 2H, 5.94, m, 1H, 5.21, dxd, 1H, 5.14, dxd, 1H, 4.98, t, 1H, 3.67, m, 2H, 3.56, m, 2H, 2.73, m, 2H, 2.47, s, 3H.

1.048 7.04, d, 1H, 7.02, t, 1H, 6.87, d, 1H, 5.05, t, 1H, 3.85, m, 2H, 3.68, m, 2H, 3.61, m, 2H, 3.43, s, 3H, 2.32, s, 3H.

1.049 7.12, m, 2H, 7.06, dxd, 1H, 5.07, t, 1H, 3.88, m, 2H, 3.62, m, 4H, 3.47, s, 3H.

1.050 7.01, m, 1H, 6.09, m, 2H, 4.98, t, 1H, 3.88, d, 2H, 3.63, m, 4H, 3.41, s, 3H.

1.051 6.84, m, 1H, 5.06, dxd, 1H, 3.89, m, 2H, 3.64, m, 4H, 3.40, s, 3H.

1.052 6.84, m, 1H, 6.79, m, 1H, 4.96, t, 1H, 3.88, d, 2H, 3.63, m, 4H, 3.41, s, 3H, 2.21, small d, 3H.

1.055 7.68, m, 1H, 6.89, m, 1H, 6.88, t, 1H, 4.99, dxd, 1H, 3.92, m, 2H, 3.63, m, 2H, 3.54, m, 4H, 1.13, t, 3H.

1.056 6.83, m, 1H, 5.06, dxd, 1H, 3.95, dxd, 1H, 3.88, dxd, 1H, 3.64, m, 2H, 3.54, m, 4H, 1.13, t, 3H.

1.057 6.84, m, 1H, 6.79, m, 1H, 4.97, dxd, 1H, 3.91, m, 2H, 3.64, m, 2H, 3.56, m, 4H, 2.21, small d, 3H, 1.16, t, 3H.

1.059 7.08, t, 1H, 6.97, d, 1H, 6.89, d, 1H, 5.08, dxd, 1H, 3.89, m, 2H, 3.63, m, 4H, 3.47, s, 3H, 2.37, s, 3H.

1.060 6.94, m, 1H, 6.91, m, 1H, 5.03, t, 1H, 3.88, m, 2H, 3.63, m, 4H, 3.39, s, 3H, 2.33, s, 3H.

1.061 7.03, d, 1H, 6.85, dxd, 1H, 5.03, t, 1H, 3.89, m, 2H, 3.67, m, 4H, 3.40, s, 3H, 2.23, s, 3H.

1.062 6.78, d, 1H, 6.63, d, 1H, 5.00, m, 1H, 3.92, dxd, 1H, 3.86, dxd, 1H, 3.65, m, 4H, 3.47, s, 3H, 2.36, s, 3H.

1.063 7.13, t, 1H, 6.93, d, 1H, 6.90, d, 1H, 5.11, m, 1H, 3.92, m, 2H, 3.64, m, 4H, 3.47, s, 3H, 2.40, s, 3H.

1.064 7.15, t, 1H, 6.91, d, 1H, 6.81, d, 1H, 5.11, m, 1H, 3.90, m, 2H, 3.68, m, 2H, 3.60, m, 2H, 3.47, s, 3H, 2.46, s, 3H.

1.065 7.11, t, 1H, 6.88, d, 1H, 6.82, d, 1H, 5.96, m, 1H, 5.20, dxd, 1H, 5.14, dxd, 1H, 4.98, t, 1H, 3.66, m, 2H, 3.56, m, 2H, 2.73, m, 2H, 2.41, s, 3H.

1.066 7.38, t, 1H, 7.22, t, 1H, 7.14, t, 1H, 5.07, m, 1H, 3.89, m, 2H, 3.66, m, 4H, 3.46, s, 3H.

1.067 7.08, t, 1H, 6.99, d, 1H, 6.87, d, 1H, 5.08, dxd, 1H, 4.04, dxd, 1H, 3.97, dxd, 1H, 3.86, m, 1H, 3.76, m, 1H, 3.64, m, 4H, 3.56, t, 2H, 3.37, s, 3H, 2.36, s, 3H.

1.069 7.03 dd 1H, 6.80 d 2H, 4.92 br s 1H, 3.82 dq 1H, 3.69-3.55 m 4H, 3.44 s 3H; 2.26 s 3H, 2.18 s 3H, 1.31 d 3H 1.070 7.00 dd 1H, 6.80 d 1H, 6.75 d 1H, 4.87 br s 1H, 3.82 m 1H, 3.72-3.54 m 4H, 3.43 s 3H, 2.28 s 3H, 2.19 s 3H, 1.28 d 3H 1.073 7.04 dd 1H, 6.90 d 1H, 6.81 d 1H, 5.84 m 1H, 5.47 dd 1H, 5.10 m 3H, 4.92 s 1H, 4.03-3.80 m 5H, 3.72 d 1H, 2.82 m 1H, 2.67 m 1H, 2.76 s 3H, 2.16 s 3H, 1.85 s 3H 1.074 7.00 dd 1H, 6.88 d 1H, 6.78 d 1H, 5.86 m 1H, 5.18 d 1H, 5.09 d 1H, 4.93 dd 1H, 4.54 ABqu 2H, 3.80 m 2H, 3.47 m 2H, 2.81 m 1H, 2.69 m 1H, 2.26 s 3H, 2.17 s 3H, 1.97 s 3H 1.075 7.00 dd 1H, 6.85 d 1H, 6.76 d 1H, 5.87 m 1H, 5.17 d 1H, 5.08 d 1H, 4.94 dd 1H, 4.83 d 1H, 4.52 d 1H, 3.79 m 2H, 3.54 m 1H, 3.44 m 1H, 3.21 s 3H, 2.80 m 1H, 2.68 m 1H, 2.24 s 3H, 2.16 s 3H 1.076 7.00 dd 1H, 6.86 d 1H, 6.76 d 1H, 6.86 m 2H, 5.24-5.06 4xd 4H, 4.96 dd 1H; 4.93 d 1H, 4.57 d 1H, 3.91 d 2H, 3.89 m 2H, 3.58 m 1H, 3.46 m 1H, 2.82 m 1H, 2.69 m 1H, 2.26 s 3H, 2.17 s 3H 1.077 7.0 t, 1H 6.8 d, 1H 6.7 d, 1H 5.8-5.9 m, 1H 5.25, dd, 1H 5.15, dd 1H 5.05, t, 1H 3.9-4.0, m, 2H, 3.7-3.85, m, 2H, 2.9-2.95, m, 1H, 2.7-2.8, m, 1H, 2.25, s, 3H, 2.12, s, 3H 1.078 7.84 d 2H, 7.63 m 1H, 7.50 dd 2H, 6.86 dd 1H, 6.76 d 1H, 6.43 d 1H, 5.95 m 1H, 5.46 dd 5.46; 5.18 d 1H, 5.10 d 1H, 3.96-3.73 m 4H, 2.82 m 1H, 2.72 m 1H, 2.23 s 3H, 2.09 s 3H 1.081 6.99 dd 1H, 6.77 d 1H, 6.63 d 1H, 5.93 m 1H, 3.80 m 4H, 2.96 dd 1H, 2.88 dd 1H, 2.23 s 3H, 2.15 s 3H, 1.50 s 9H, 1.49 s 1H 1.082 7.00 dd 1H, 6.81 d 1H, 6.72 d 1H, 5.86 m 1H, 3.86 m 4H, 3.12 dd 1H, 3.03 dd 1H, 2.26 s 3H, 2.22 s 3H, 1.48 s 9H 1.083 6.97 dd 1H, 6.75 d 1H, 6.46 d 1H, 5.50 m 1H, 3.76 m 4H, 3.61 m 2H, 2.25 s 3H, 2.22 s 3H, 2.17-2.03 m 4H, 1.53 s 9H 1.084 6.98, t, 1H 6.75, d, 1H 6.62, d, 1H 5.83, m, 1H 4.61-4.70, dd, 1H, 4.42-4.48, dd, 1H, 3.70-3.85, m, 4H, 2.22, s, 3H, 2.19, s, 3H, 2.05, s, 3H, 1.49, s, 9H 1.085 6.99 dd 1H, 6.79 d 1H, 6.54 d 1H, 5.80 m 1H, 3.82 m 4H, 3.76 dd 1H, 3.68 dd 1H, 2.26 s 3H, 2.23 s 3H, 1.52 s 9H 1.086 7.00 dd 1H, 6.80 d 1H, 6.62 d 1H, 5.81 m 1H, 4.03 dd 1H, 3.93 dd 1H, 3.82 m 4H, 2.26 s 3H, 2.23 s 3H, 1.50 s 9H 1.087 8.50 s 1H, 6.96 dd 1H, 6.78 d 1H, 6.52 d 1H, 6.27 m 1H, 5.32 dd 1H, 5.22 dd 1H, 3.82 m 4H, 2.20 s 3H, 2.04 s 3H, 1.52 s 9H 1.088 7.00 dd 1H, 6.77 d 1H, 6.69 d 1H, 6.70 m 1H, 6.63 m 1H, 5.56 d 1H, 5.33 d 1H, 3.32 m 4H, 2.26 and 2.23 2s 2×3H, 1.47 s 9H Compounds of the invention can be prepared by a variety of methods, for example those described below.

Compounds of the formula I wherein Z is not H can be prepared from compounds of the formula I in which Z is H, by treatment with the appropriate reagent.

Depending on the nature of Z this can be for example an alkylating agent, an acylating agent, a phosphorylating agent, a carbamoylating agent, a sulfenylating agent or an oxidising agent. These derivatisating agents are generally electrophiles. Methods for the conversion of NH groups into NZ groups can be found for example in T. W. Greene and P. G. M. Wuts "Protecting Groups in Organic Synthesis" 3$^{rd}$ Edition, Wiley, NY 1999. Similarly if the group $R^1$ contains a reactive moiety, compounds of the formula I bearing such an $R^1$ group can be converted into other compounds of the formula I, by means of chemical transformation of the reactive moiety in group $R^1$.

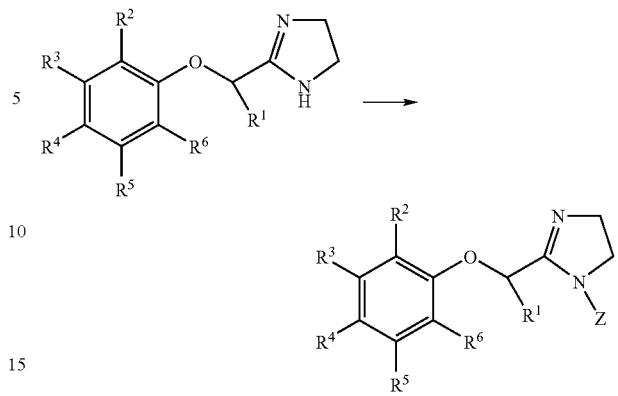

Compounds of the formula I can be prepared by alkylation of a phenol of the formula 2, with a 2-haloalkylimidazoline of the formula 3 (J. Am. Chem. Soc. 1947, 69, 1688).

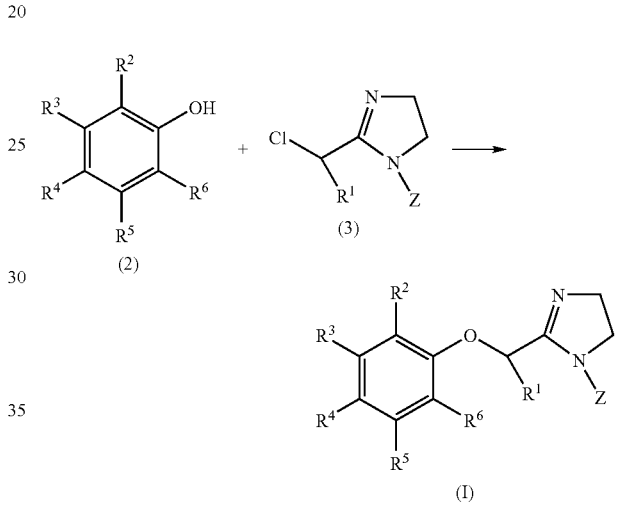

Compounds of the formula I can be prepared from nitriles of the formula 4, by treatment with a diamine of the formula 5. This is advantageously performed in the presence of a catalyst such as $CS_2$, $P_2S_5$ (J. Med. Chem., 2003 46, 1962) or $Na_2S_4$ (DE 2512513). The nitrile 4 can be converted to imidates of the formula 6 using an alcohol such as ethanol and an acid such as HCl. Imidates of the formula 6 can be converted to compounds of the formula I on treatment with diamines of the formula 5 (J. Med. Chem., 2004, 47, 6160; J. Am. Chem. Soc. 1947, 69, 1688). Nitriles of the formula 4 can be prepared by alkylating phenols of the formula 2 with a nitrile of the formula 9, bearing a leaving group $L_1$ (J. Am. Chem. Soc. 1947, 69, 1688).

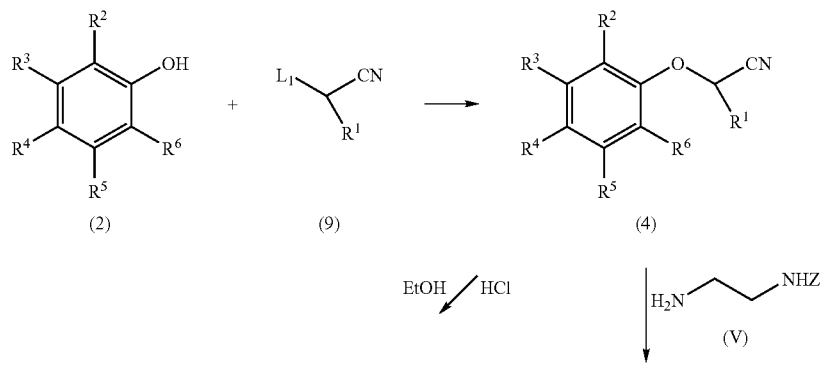

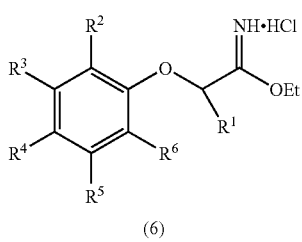 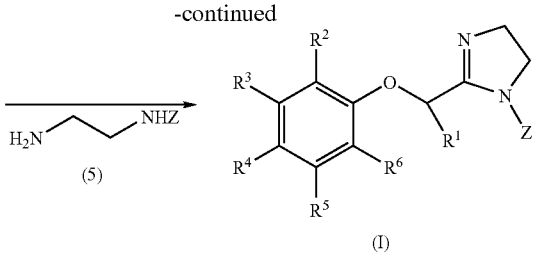

Esters of the formula 7 can be converted to imidazolines of the formula I by treatment with diamines of the formula 5 (J. Am. Chem. Soc. 1950, 72, 4443-5). Alkylaluminium reagents can be used with advantage to facilitate this reaction. This conversion occurs in two steps by forming first the monoamide 11, which can serve as a precursor to imidazolines of the formula I. Esters of the formula 7 can be prepared by alkylation of phenols of the formula 2 with esters of the formula 10, wherein $L_2$ is a leaving group, and $R^{21}$ is an optionally substituted alkyl or aryl group (typically $C_1$-$C_6$ alkyl, phenyl or benzyl). The leaving groups $L_1$ and $L_2$ are typically those used for $S_N2$ reactions. $L_1$ and $L_2$ become anions of organic or inorganic acids on leaving their substrates 9 and 10. Typical leaving groups are for example halides such as chloride or bromide, alkylsulfonates such as mesylate, and arylsulfonates such as tosylate.

removed if desired, and a different Z group can be attached as described above if so desired.

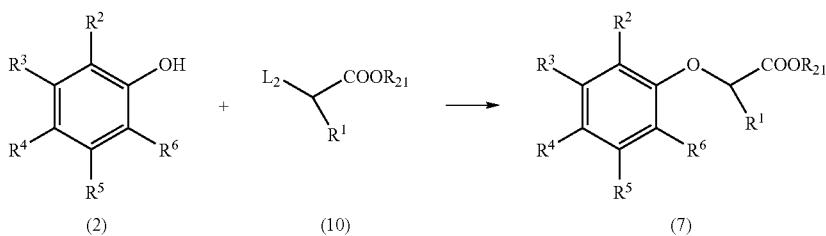

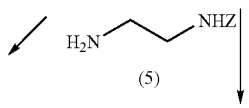

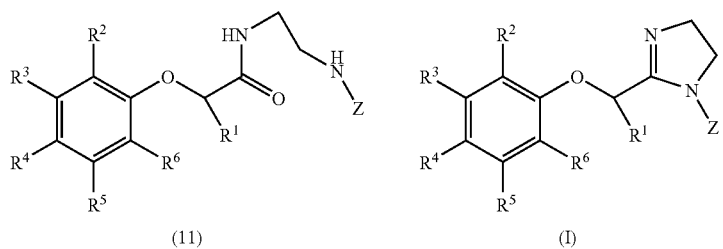

Compounds of the formula I can be prepared from imidazolines of the formula (8) by introduction of a group $R^1$. This can be done by treating 8 with a base and then subsequently with an electrophile capable of introducing the group $R^1$. A typical electrophile could be a halide such as $R^1$—Cl, $R^1$—Br, or $R^1$—I. A typical base could be mesityl-lithium. This process is exemplified in Examples 2 and 4. The Z group can be a protecting group such as tBuOCO, which can be -continued

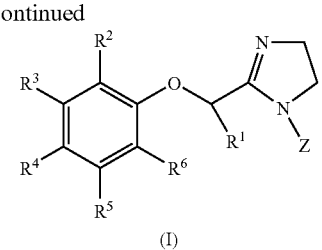

The compound 3-(4,5-dihydro-1H-imidazol-2-yl)-3-(2,6-dimethyl-phenoxy)-propan-1-ol may be prepared as described by Moormann et al. supra.

Compounds of formula (2), (3), (5), (7), (8), (9) and (10) are known compounds or may be obtained readily from known compounds using processes that are routine in the art and with which the skilled man will be familiar.

Nitriles of the formula (9), and especially nitriles for the formula (9a), wherein $L_1$ is an alkylsulfonyl or an arylsulfonyl group, may be obtained from the corresponding aldehydes by first treating with an alkali cyanide or with trimethylsilylcyanide to form a cyanohydrin of the formula (12) and then treating the cyanohydrin (12) with an alkylsulfonylchloride or an arylsulfonylchloride and a base like triethylamine or pyridine to form the sulfonylcyanide (9a). The preparation of such nitriles of the formula (IX) in their chiral form is described for examples in Chemische Berichte, 126, 779 (1993).

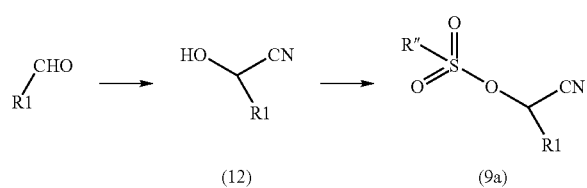

The compounds of the formula (4), wherein $R^1$, $R^2$, $R^3$, $R^4$, $R^5$ and $R^6$ are as described in formula I above, have been specifically designed as intermediates for the synthesis of the compounds of the formula I and are part of this invention.

TABLE 4

Characterising data for intermediate compounds of the invention (4)

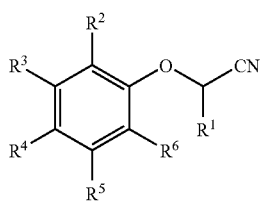

| Compound No | $R^1$ | $R^2$ | $R^3$ | $R^4$ | $R^5$ | $R^6$ | Physical Remarks data*) |
|---|---|---|---|---|---|---|---|
| 4.041 | allyl | F | F | H | F | H | Oil |
| 4.042 | allyl | F | H | H | H | F | Oil |
| 4.043 | allyl | F | F | H | F | F | Oil |
| 4.044 | allyl | Me | F | H | F | H | Oil |
| 4.045 | allyl | Me | F | H | H | F | Oil |
| 4.046 | allyl | Me | Cl | H | H | H | Oil |
| 4.047 | allyl | Cl | Me | H | H | H | Oil |
| 4.048 | MeOCH$_2$— | Me | Cl | H | H | H | Oil |
| 4.049 | MeOCH$_2$— | Cl | Cl | H | H | H | Oil |
| 4.050 | MeOCH$_2$— | F | H | H | H | F | Oil |
| 4.051 | MeOCH$_2$— | F | F | H | F | F | Oil |
| 4.052 | MeOCH$_2$— | F | Me | H | H | F | Oil |
| 4.053 | EtOCH$_2$— | Me | Cl | H | H | H | Oil |
| 4.054 | EtOCH$_2$— | Cl | Cl | H | H | H | Oil |
| 4.055 | EtOCH$_2$— | F | H | H | H | F | Oil |
| 4.056 | EtOCH$_2$— | F | F | H | F | F | Oil |
| 4.057 | EtOCH$_2$— | F | Me | H | H | F | Oil |
| 4.058 | EtOCH$_2$— | Cl | Me | H | H | H | Oil |
| 4.059 | MeOCH$_2$— | Cl | Me | H | H | H | Oil |
| 4.060 | MeOCH$_2$— | Cl | Me | H | F | H | Oil |
| 4.061 | MeOCH$_2$— | F | Me | H | H | Cl | Oil |
| 4.062 | MeOCH$_2$— | Cl | Me | H | F | H | Oil |
| 4.063 | MeOCH$_2$— | Br | Me | H | H | H | Oil |
| 4.064 | MeOCH$_2$— | I | Me | H | H | H | Oil |
| 4.065 | allyl | Br | Me | H | H | H | Oil |
| 4.066 | MeOCH$_2$— | F | CF$_3$ | H | H | H | Oil |
| 4.067 | MeOCH$_2$CH$_2$OCH$_2$— | Cl | Me | H | H | H | Oil |
| 4.068 | allyl | Me | F | H | H | H | Oil |
| 4.069 | MeOCH$_2$— | Me | F | H | H | H | Oil |
| 4.070 | MeOCH$_2$— | Cl | CF$_3$ | H | H | H | Oil |
| 4.071 | cyclopropyl | Me | Me | H | H | H |  |
| 4.072 | cyclobutyl | Me | Me | H | H | H |  |

*$^1$H-NMR (CDCl$_3$) of selected compounds:
4.041 6.75 to 6.65, 2H; 5.99, m, 1H; 5.36, dxd, 1H; 5.32, dxd, 1H; 4.79, t, 1H; 2.89, m, 2H.
4.042 7.09, m, 1H; 6.96, m, 2H; 5.94, m, 1H; 5.36, dxd, 1H; 5.34, dxd, 1H; 4.88, t, 1H; 2.78, m, 2H.
4.043 6.94, m, 1H; 5.92, m, 1H; 5.38, dxd, 1H; 5.35, dxd, 1H; 4.97, t, 1H; 2.87, dxd, 2H.
4.044 6.58 to 6.52, 2H; 5.92, m, 1H; 5.36, dxd, 1H; 5.34, dxd, 1H; 4.75, t, 1H; 2.85, dxd, 2H; 2.08, small d, 3H.
4.045 6.93, m, 1H; 6.82, m, 1H; 5.95, m, 1H; 5.37, dxd, 1H; 5.34, dxd, 1H; 4.92, t, 1H; 2.83, m, 2H; 2.27, small d, 3H.
4.046 7.15 to 7.10, 2H; 7.02, d, 1H; 6.91, dxd, 1H; 5.93, m, 1H; 5.36, dxd, 1H; 5.33, dxd, 1H; 4.77, t, 1H; 2.84, t, 2H; 2.39, s, 3H.
4.047 7.15, t, 1H; 7.02, d, 1H; 7.00, d, 1H; 5.96, m, 1H; 5.36, dxd, 1H; 5.32, dxd, 1H; 4.80, t, 1H; 2.86, t, 2H; 2.39, s, 3H.
4.049 7.45, d, 1H; 7.39, m, 1H; 7.23, t, 1H; 4.94, t, 1H; 3.96, d, 2H; 3.56, s, 3H.
4.050 7.12, m, 1H; 6.96, m, 2H; 5.01, t, 1H; 3.93, m, 2H; 3.54, s, 3H.
4.051 6.95, m, 1H; 5.08, t, 1H; 3.94, m, 2H; 3.52, s, 3H.
4.052 6.94, m, 1H; 6.85, m, 1H; 4.98, t, 1H; 3.92, m, 2H; 3.54, s, 3H; 2.25, small d, 3H.
4.054 7.30 to 7.20, 2H; 7.09, d, 1H; 4.92, t, 1H; 4.00, d, 2H; 3.72, q, 2H; 1.25, t, 3H.
4.055 7.10, m, 1H; 6.96, m, 2H; 5.00, t, 1H; 3.95, m, 2H; 3.68, m, 2H; 1.25, t, 3H.
4.056 6.94, m, 1H; 5.07, dxd, 1H; 3.96, m, 2H; 3.67, m, 2H; 1.23, t, 3H.
4.057 6.94, m, 1H; 6.84, m, 1H; 4.98, t, 1H; 3.96, m, 2H; 3.68, m, 2H; 2.27, small d, 3H; 1.25, t, 3H.
4.060 7.08 to 6.95, 2H; 5.03, m, 1H; 3.93, m, 2H; 3.54, s, 3H; 2.35, s, 3H.
4.061 7.09, d, 1H; 6.95, dxd, 1H; 5.02, t, 1H; 3.94, m, 2H; 3.54, s, 3H; 2.27, small d, 3H.
4.065 7.21, t, 1H; 7.03, d, 1H; 6.96, d, 1H; 5.98, m, 1H; 5.36, dxd, 1H; 5.32, dxd, 1H; 4.80, t, 1H; 2.88, m, 2H; 2.42, s, 3H.
4.066 7.33 to 7.22, 3H; 4.98, t, 1H; 3.95, d, 2H; 3.54, s, 3H.
4.067 7.16, t, 1H; 7.02, d, 1H; 7.00, d, 1H; 4.96, t, 1H; 4.08, m, 2H; 3.85, d, 2H; 4.60, m, 2H; 3.40, s, 3H; 2.48, s, 3H.
4.068 7.16, dxd, 1H; 6.79, t, 1H; 6.78, d, 1H; 5.92, m, 1H; 5.36, dxd, 1H; 5.32, dxd, 1H; 4.79, t, 1H; 2.84, m, 2H; 2.15, small d, 3H.
4.069 7.15, dxd, 1H; 6.82, t, 1H; 6.80, d, 1H; 4.91, t, 1H; 3.92, m, 2H; 3.52, s, 3H; 2.17, small d, 3H.
4.070 7.52 to 7.30, 3H; 4.95, t, 1H; 3.98, m, 2H; 3.55, s, 3H.
4.071 7.07 dd 1H; 6.91 d 1H; 6.84 d 1H; 4.47 d 1H; 2.39 s 3H; 2.18 s 3H; 1.57 m 1H; 0.80 m 2H; 0.67 m 2H
4.072 7.09 dd 1H; 6.89 d 1H; 6.84 d 1H; 4.66 d 1H; 3.01 m 1H; 2.28 s 3H; 2.17 s 3H; 2.26-1.95 m 6H The compounds of formula (I) and 3-(4,5-dihydro-1H-imidazol-2-yl)-3-(2,6-dimethyl-phenoxy)-propan-1-ol can be used to combat and control infestations of insect pests such as Lepidoptera, Diptera, Hemiptera, Thysanoptera, Orthoptera, Blattodea, Coleoptera, Siphonaptera, Hymenoptera and lsoptera and also other invertebrate pests, for example, acarid, nematode and mollusc pests. Insects, acarids, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (1) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides fells* (cat flea), *Lirionlyza* spp. (ieafminer), *Musca domestics* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus*, and *R. santonensis*) and the *Termitidae* (for example *Globitermes sulphureus*), *Solenopsis geminata* (fire ant), *Monomorium pharaonis* (pharaoh's ant), *Damalinia* spp. and *Linognathus* spp. (biting and sucking lice), and *Deroceras reticulatum* (slug).

The invention therefore provides a method of combating and controlling insects, acarid, or molluscs which comprises applying an insecticidany, acaricidally, nernaticidaily or molluscicidally effective amount of a compound of formula (I) or 3-(4,5-dihydro-1H-imidazol-2-yl)-3-(2,6-dimethyl-phenoxy)-propan-1-ol, or a composition containing a compound of formula (I) or 3-(4,5-dihydro-1H-imidazol-2-yl)-3-(2,6-dimethyl-phenoxy)-propan-1-ol, to a pest, a locus of pest, or to a plant susceptible to attack by a pest. The compounds of formula (I) and/or 3-(4,5-dihydro-1H-imidazol-2-yl)-3-(2,6-dimethyl-phenoxy)-propan-1-ol, as well as compositions comprising these compounds, are preferably used against insects or acarids.

In particularly preferred embodiments 3-(4,5-dihydro-1H-imidazol-2-yl)-3-(2,6-dimethyl-phenoxy)-propan-1-ol, compounds of formula (I) and compositions containing such compounds are used in methods of controlling and combating an insects in the orders Hemiptera, Lepidoptera, Coleoptera, Thysanoptera, Diptera, Blattodea, Isoptera, Siphonaptera, Hymenoptera, and/or Orthoptera. In certain embodiments, such compounds and compositions are particularly useful in controlling and combating Hemiptera, Lepidoptera, Coleoptera, Thysanoptera, or Diptera. In further embodiments such compounds and compositions are particularly useful in controlling and combating Lepidoptera, Thysanoptera, Isoptera, Siphonaptera, Hymenoptera, or Orthoptera. It is particularly preferred that 3-(4,5-dihydro-1H-imidazol-2-yl)-3-(2,6-dimethyl-phenoxy)-propan-1-ol and/or compounds of formula (I), and composition containing these compounds are used against Hemipteran insects.

The term "plant" as used herein includes seeds, seedlings, bushes and trees. In order to apply a compound of formula (I) or 3-(4,5-dihydro-1H-imidazol-2-yl)-3-(2,6-dimethyl-phenoxy)-propan-1-ol as an insecticide, acaricide, nematicide or molluscicide to a pest, a locus of pest, or to a plant susceptible to attack by a pest, the compound is usually formulated into a composition which includes, in addition to the compound of formula (I) or 3-(4,5-dihydro-1H-imidazol-2-yl)-3-(2,6-dimethyl-phenoxy)-propan-1-ol, a suitable inert diluent or carrier and, optionally, a surface active agent (SFA). Suitable inert diluents or carriers are described herein, for example with respect to certain formulation types, and thus the term includes solid diluents, inorganic water soluble salts, water-soluble organic solids and the like as well as simple diluents such as, for example, water and/or oils. SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of 3-(4,5-dihydro-1H-imidazol-2-yl)-3-(2,6-dimethyl-phenoxy)-propan-1-ol or of a compound of formula (I). The composition is generally used for the control of pests such that 3-(4,5-dihydro-1H-imidazol-2-yl)-3-(2,6-dimethyl-phenoxy)-propan-1-ol or a compound of formula (I) is applied at a rate of from 0.1 g to 10 kg per hectare, preferably from 1 g to 6 kg per hectare, more preferably from 1 g to 1 kg per hectare.

When used in a seed dressing, 3-(4,5-dihydro-1H-imidazol-2-yl)-3-(2,6-dimethyl-phenoxy)-propan-1-ol or a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of 3-(4,5-dihydro-1H-imidazol-2-yl)-3-(2,6-dimethyl-phenoxy)-propan-1-ol or a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition as described hereinbefore. Such compositions are preferably used against insects, acarines or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the pesticidally active ingredient i.e. 3-(4,5-dihydro-1H-imidazol-2-yl)-3-(2,6-dimethyl-phenoxy)-propan-1-ol or a compound of formula (I).

Dustable powders (DP) may be prepared by mixing the pesticidally active ingredient with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing the pesticidally active ingredient with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing the pesticidally active ingredient with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of the pesticidally active ingredient and one or more powdered solid diluents or carriers, or from pre-formed blank granules by absorbing the pesticidally active ingredient (or a solution thereof, in a suitable agent) in a porous granular material (such as pumice, attapulgite clays, fuller's earth, kieselguhr, diatomaceous earths or ground corn cobs) or by adsorbing the pesticidally active ingredient (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving the pesticidally active ingredient in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving the pesticidally active ingredient in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining the pesticidally active ingredient either as a liquid (if it is not a liquid at room temperature, it may be melted at a reasonable temperature, typically below 70° C.) or in solution (by dissolving it in an appropriate solvent) and then emulsifiying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. The pesticidally active ingredient is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of the pesticidally active ingredient. SCs may be prepared by ball or bead milling the solid compound of formula (I) in a suitable medium, optionally with one or more dispersing agents, to produce a fine particle suspension of the compound. One or more welting agents may be included in the composition and a suspending agent may be included to reduce the rate at which the particles settle. Alternatively, the pesticidally active ingredient may be dry milled and added to water, containing agents hereinbefore described, to produce the desired end product.

Aerosol formulations comprise the pesticidally active ingredient and a suitable propellant (for example n-butane). The pesticidally active ingredient may also be dissolved or dispersed in a suitable medium (for example water or a water miscible liquid, such as n-propanol) to provide compositions for use in non-pressurised, hand-actuated spray pumps.

The pesticidally active ingredient may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains the pesticidally active ingredient and, optionally, a carrier or diluent therefor. The polymeric shell may be produced by either an interfacial polycondensation reaction or by a coacervation procedure. The compositions may provide for controlled release of the compound of formula (I) and they may be used for seed treatment. The pesticidally active ingredient may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of the pesticidally active ingredient). Such additives include surface active agents, spray additives based on oils, for example certain mineral oils or natural plant oils (such as soy bean and rape seed oil), and blends of these with other bio-enhancing adjuvants (ingredients which may aid or modify the action of the pesticidally active ingredient). In particularly preferred embodiments, compounds of formula I will be formulated as an EC or EW formulation.

A compound of formula (I) or 3-(4,5-dihydro-1H-imidazol-2-yl)-3-(2,6-dimethyl-phenoxy)-propan-1-ol may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

Compounds of formula (I) and/or 3-(4,5-dihydro-1H-imidazol-2-yl)-3-(2,6-dimethyl-phenoxy)-propan-1-ol may be applied by any of the known means of applying pesticidal compounds. For example, they may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or they may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

Compounds of formula (I) or 3-(4,5-dihydro-1H-imidazol-2-yl)-3-(2,6-dimethyl-phenoxy)-propan-1-ol may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

Compounds of formula (I) and 3-(4,5-dihydro-1H-imidazol-2-yl)-3-(2,6-dimethyl-phenoxy)-propan-1-ol (either individually or in combination with each other) may be used in mixtures with fertilisers (for example nitrogen-, potassium- or phosphorus-containing fertilisers). Suitable formulation types include granules of fertiliser. The mixtures suitably contain up to 25% by weight of the compound of formula (I) or 3-(4,5-dihydro-1H-imidazol-2-yl)-3-(2,6-dimethyl-phenoxy)-propan-1-ol.

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) or 3-(4,5-dihydro-1H-imidazol-2-yl)-3-(2,6-dimethyl-phenoxy)-propan-1-ol may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I) or 3-(4,5-dihydro-1H-imidazol-2-yl)-3-(2,6-dimethyl-phenoxy)-propan-1-ol; or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Chloronicotinyl compounds such as imidacloprid, thiacloprid, acetamiprid, nitenpyram or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr; or q) Pymetrozine, in particular pymetrozine dihydrate.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoro-methyl-benzimidazole-1-sulphonamide, α-[N-(3-chloro-2,6-xylyl)-2-methoxy-acetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)-propionamide (AC382042), N-(2-methoxy-5-pyridyl)-cyclo-propane carboxamide, acibenzolar (CGA245704), alanycarb, aldimorph, anilazine, azaconazole, azoxystrobin, benalaxyl, benomyl, bi-loxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N-([methyl (methyl-thioethylideneamino-oxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-iso-propyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) and/or 3-(4,5-dihydro-1H-imidazol-2-yl)-3-(2,6-dimethyl-phenoxy)-propan-1-ol may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

Various aspects and embodiments of the present invention will now be illustrated in more detail by way of example. It will be appreciated that modification of detail may be made with out departing from the scope of the invention.

For the avoidance of doubt, where a literary reference, patent application, or patent, is cited within the text of this application, the entire text of said citation is herein incorporated by reference.

EXAMPLES

Example 1

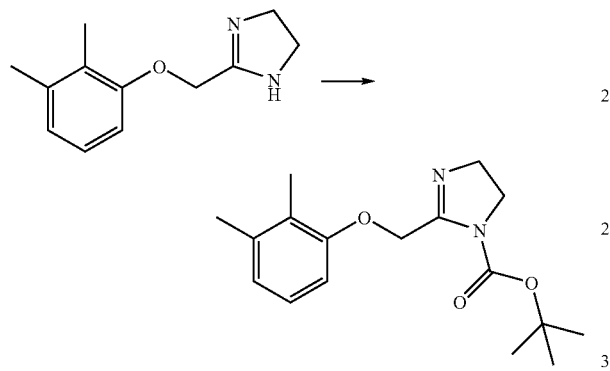

BOC-anhydride (12.3 g, 56.3 mmol) was added in portions to a solution of 2-(2,3-dimethyl-phenoxymethyl)-4,5-dihydro-1H-imidazole (10 g, 49 mmol) and triethylamine (7.8 ml, 56.3 mmol, 5.6 g) in 100 ml dichloromethane under nitrogen with cooling with a cold water bath, giving an exothermic reaction with each addition. The reaction was then left for 2 hours and shaken between dichloromethane and water. The organic phase was dried with $Na_2SO_4$ and evaporated to give 2-(2,3-Dimethyl-phenoxymethyl)-4,5-dihydro-imidazole-1-carboxylic acid tert-butyl ester as a white crystalline solid (m.p. 102-108° C.).

Example 2

This example illustrates the preparation of compound No X-76

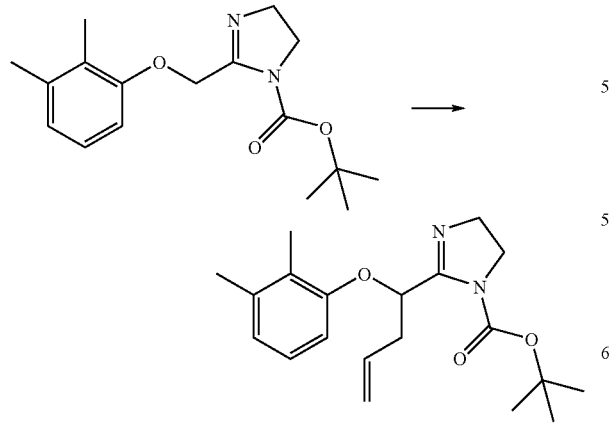

A solution of t-butyllithium in pentane (1.7M, 5.7 ml, 9.84 mmol) was added in portions to a solution of 2,4,6-trimethylphenylbromide (0.744 ml, 980 mg, 4.93 mmol) in 8 ml THF at ca −78° C. A white precipitate was formed. After 10 minutes at low temperature a solution of 2-(2,3-dimethyl-phenoxymethyl)-4,5-dihydro-imidazole-1-carboxylic acid tert-butyl ester (1 g, 3.28 mmol) in 6 ml THF was added in portions to give an orange solution. This was warmed to −20° C. and cooled again to ca −70° C. whereupon much of the solid went into solution. Allyl bromide (0.332 ml, 475 mg, 3.93 mmol) was added and the reaction mixture stirred for 30 min at this temperature before a small amount of acetic acid was added. The mixture was warmed and shaken between EtOAc and water. The organic phase was dried with $Na_2SO_4$ and evaporated to give 1.3 g of crude product, which was chromatographed on silica to yield 2-[1-(2,3-dimethyl-phenoxy)-but-3-enyl]-4,5-dihydro-imidazole-1-carboxylic acid tert-butyl ester. $^1$H-NMR (CDCl$_3$) (selection) 5.10 (d, allyl), 5.18 (d, allyl), 5.66 (t, OCH), 5.98 (m, allyl)

Example 3

This example illustrates the preparation of compound No I-50

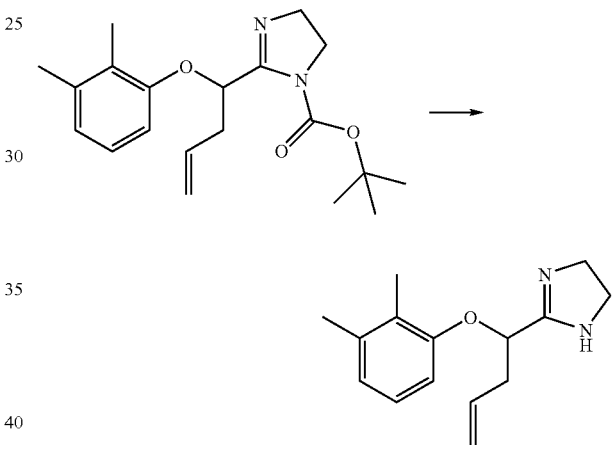

2-[1-(2,3-dimethyl-phenoxy)-but-3-enyl]-4,5-dihydroimidazole-1-carboxylic acid tert-butyl ester (120 mg) was dissolved in a solution of 10% trifluoroacetic acid in dichloromethane (5 ml). After 24 hours the mixture was shaken between NaOH (2M) and EtOAc and the organic phase dried with $Na_2SO_4$ and evaporated to yield 2-[1-(2,3-Dimethyl-phenoxy)-but-3-enyl]-4,5-dihydro-1H-imidazole as crystals m.p. 72-74° C.

Example 4

2-[1-(2,3-Dimethyl-phenoxy)-but-3-ynyl]-4,5-dihydro-imidazole-1-carboxylic acid tert-butyl ester (compound No XVII-76) was prepared following the method described in example 2 using propargyl bromide.

Example 5

2-[1-(2,3-Dimethyl-phenoxy)-but-3-ynyl]-4,5-dihydro-1H-imidazole (compound No I-106) was prepared from the product of example 4 using the method described in example 3. It had m.p. 70-73° C.

Example 6

2-[1-(2,3-Dimethyl-phenoxy)-3-fluoro-propyl]-4,5-dihydro-imidazole-1-carboxylic acid tert-butyl ester (compound No 1.006) was prepared following the method described in example 2 using 1-bromo-2-fluoro-ethane.

Example 7

2-[1-(2,3-Dimethyl-phenoxy)-3-fluoro-propyl]-4,5-dihydro-1H-imidazole (compound No 3) was prepared from the product of example 6 using the method described in example 3. It had m.p. 107-109° C.

Example 8

This example illustrates the preparation of compound No 1.059

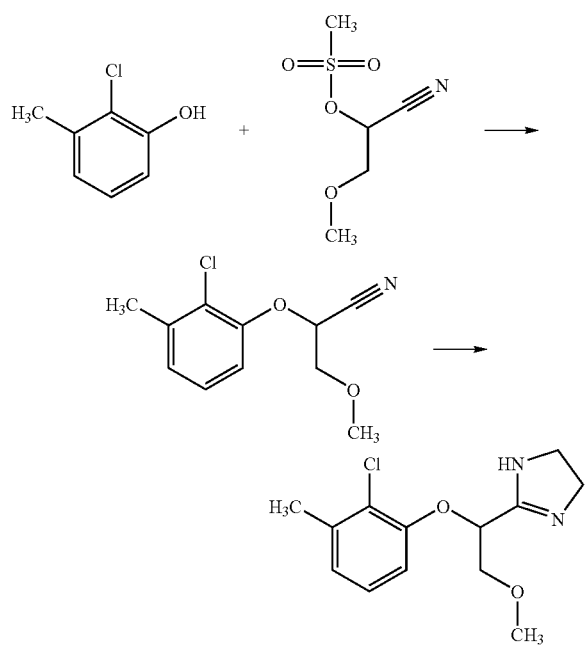

A: 142 mg (1 mMol) 2-chloro-3-methyl-phenol and 224 mg (1.25 mMol) methanesulfonic acid 1-cyano-2-methoxy-ethyl ester were heated in the presence of 175 mg (1.25 mMol) $K_2CO_3$ in 8 ml acetonitrile for 4 hours to refluxing temperature. The cooled mixture was extracted with tert.-butylmethylether and a 2N NaOH solution, dried and evaporated. The residue was purified by silica chromatography (eluent: cyclo-hexane/ethylacetate 9:1) to get as an oil 2-(2-chloro-3-methyl-phenoxy)-3-methoxy-propionitrile; $^1$H-NMR ($CDCl_3$): 7.30 to 7.00, 3 aromatic H, 4.92, t, 1H, 3.95, d, 2H, 3.55, s, 3H, 2.39, s, 3H.

B: 35 mg (0.16 mMol) of 2-(2-chloro-3-methyl-phenoxy)-3-methoxy-propionitrile and 85 mg (1.4 mMol) ethylendiamine were heated in the presence of a catalytic amount of $Na_2S_4$ in 5 ml methanol for 4 hours to refluxing temperature. The solvent was evaporated and the residue extracted with dichloromethane against water, dried and evaporated. After flash-chromatography (eluent: ethylacetate/methanol/triethylamine 95:2.5:2.5) pure 2-[1-(2-chloro-3-methyl-phenoxy)-2-methoxy-ethyl]-4,5-dihydro-1H-imidazole was obtained as a resin; $^1$H-NMR ($CDCl_3$): 7.08, t, 1H, 6.97, d, 1H, 6.89, d, 1H, 5.08, dxd, 1H, 3.89, m, 2H, 3.70 to 3.55, b m, 4H, 3.47, s, 3H, 2.37, s, 3H.

Example 9

This example illustrates the preparation of methanesulfonic acid 1-cyano-2-methoxy-ethyl ester:

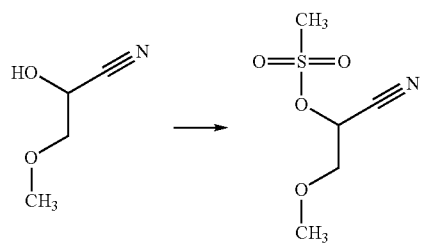

27.3 gr (0.27 Mol) of 2-hydroxy-3-methoxy-propionitrile was dissolved dichloromethane (250 ml) and treated first with 56.4 ml (0.40 Mol) triethylamine keeping the temperature below −8° C., followed by dropwise addition of 23.1 ml (0.297 mol) methansulfonyl chloride keeping the temperature below +7° C. under cooling. After the exothermic reaction ceased the mixture was left to reach room-temperature. Water was stirred in, and the mixture was extracted with tert.-butylmethylether, washed with brine, dried and evaporated. To remove some polar side-products the crude liquid obtained was filtered through silica gel (eluent: cyclohexane/ethylacetate 1:1). Methanesulfonic acid 1-cyano-2-methoxy-ethyl ester of 89% purity (GC-MS) was obtained; $^1$H-NMR ($CDCl_3$): 5.33, t, 1H, 3.81, d, 2H, 3.48, s, 3H, 3.21, s, 3H.

Example 10

Methanesulfonic acid 1-cyano-2-ethoxy-ethyl ester was prepared following the method described in example 9 $^1$H-NMR ($CDCl_3$): 5.32, t, 1H, 3.84, d, 2H, 3.63, m, 3H, 3.20, s, 3H, 1.23, s, 3H.

Example 11

Methanesulfonic acid 1-cyano-2-(2-methoxy-ethoxy)-ethyl ester was prepared following the method described in example 9; $^1$H-NMR ($CDCl_3$): 5.37, t, 1H, 3.95, d, 2H, 3.76, m, 2H, 3.56, m, 2H, 3.38, s, 3H, 3.20, s, 3H.

Example 12

This example illustrates the preparation of compound No 4.045

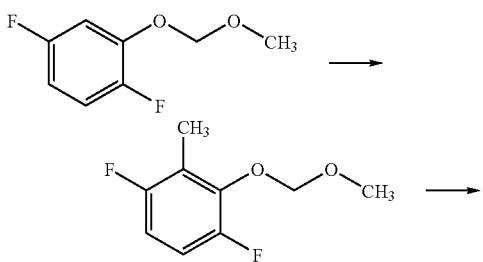

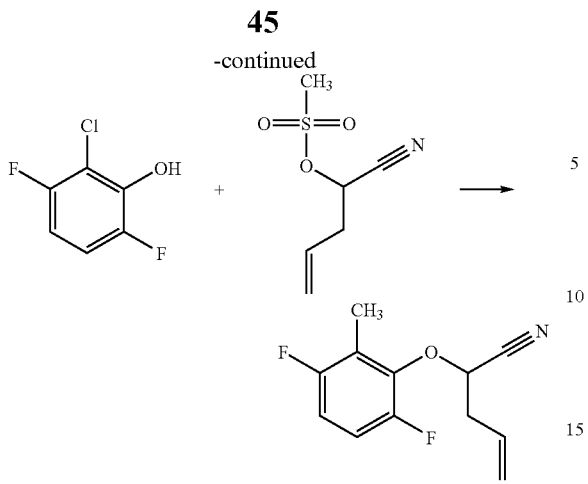

B: 2.45 gr (14.1 mMol) 1,4-difluoro-2-methoxymethoxy-benzene (obtained following Synthesis 2004(10), 1609, by treating 2,5-difluorophenol with chloromethyl-methyl-ether and Hünig's base in dichloromethane) were dissolved in dry tetrahydrofuran (25 ml) and cooled to –78° C. 12.3 ml of a 1.6N solution of n-butyllithium in n-hexane (19.7 mMol) was dropped in under temperature control of –60° C. After stirring for another 4.5 hours at –78° C. the reaction was quenched by the drop-wise addition of 12 gr (84 mMol) methyliodide dissolved in tetrahydrofuran (15 ml) and holding the reaction temperature below –60° C. After the addition the reaction mixture was allowed to reach room-temperature, and the solvents were removed under reduced pressure. The residue was extracted with ethylacetate against water, dried and evaporated. After filtration through a short column of silica gel (eluent; cyclohexane/ethylacetate 9:1) pure 1,4-difluoro-2-methoxymethoxy-3-methyl-benzene was obtained as colourless oil; $^1$H-NMR (CDCl$_3$): 6.87, dxdxd, 1H, 6.73, dxdxd, 1H, 5.13, s, 2H, 3.58, s, 3H, 2.22, small d, 3H.

C: 0.82 gr (4.4 mMol) of the product obtained in B was heated in a mixture of conc. HCl (3 ml) and iso-propanol (6 ml) for 1 hour at 75° C. The cooled reaction mixture was basidified with 2N NaOH and extracted once with diethylether that was discarded. The basic aqueous phase was acidified with conc. HCl and ice and extracted with dichloromethane. The organic phase was dried over Na$_2$SO$_4$, and the solvent was evaporanted at 40° C. and 600 mbar to leave as oil 3,6-difluoro-2-methyl-phenol; $^1$H-NMR (CDCl$_3$): 6.86, dxdxd, 1H, 6.53, dxdxd, 1H, 6.30, b, OH; 2.18, small d, 3H.

D: 200 mg (1.39 mMol) of crude product obtained in C and 270 mg (1.53 mMol) methanesulfonic acid 1-cyano-but-3-enyl ester were heated in the presence of 240 mg (1.25 mMol) K$_2$CO$_3$ in 4 ml acetonitrile for 4 hours to refluxing temperature. After checking the reaction by TLC another 270 mg (1.53 mMol) methanesulfonic acid 1-cyano-but-3-enyl ester was added, and heating was continued for 2 hours. The cooled mixture was diluted with water and extracted with tert.-butylmethylether, dried over Na$_2$SO$_4$ and evaporated. The residue was purified by flash chromatography (eluent: cyclo-hexane/ethylacetate 6:1) to leave as an oil 2-(3,6-difluoro-2-methyl-phenoxy)-pent-4-enenitrile; $^1$H-NMR (CDCl$_3$): 6.93, dxdxd, 1H, 6.82, dxdxd, 1H, 5.95, m, 1H, 5.36, dxd, 1H, 5.34, dxd, 1H, 4.92, t, 1H, 2.83, m, 2H, 2.27, small d, 3H.

Example 13

This example illustrates the preparation of methanesulfonic acid 1-cyano-but-3-enyl ester:

A: Similar to a procedure described in Eur. J. Org. Chem. 1672 (2006) 3 gr (41.6 mMol) 3-buten-1-ol were dissolved in a 9:1 mixture of pentane and dichloromethane (210 ml). Under well-stirring 0.65 gr (41.6 mMol) TEMPO (tetramethylpiperidine-N-oxid) was added at once followed by careful addition of 14.7 gr (45.8 mMol) iodobenzene-diacetate. Stirring was continued at room temperature for about 2 hours. When checked by TLC no starting material could be detected anymore, a saturated NaHCO$_3$ solution (100 ml) was stirred in under evolution of CO$_2$ and a 2-phase system containing 3-but-enal in the organic phase was obtained (solution A). In a separate vessel a HCN solution was prepared by dissolving 6.11 gr (0.125 Mol) sodium cyanide in 45 ml water and neutralisation with a 0.1 molar citrate buffer solution to reach pH 4.8 (solution B). To the 2-phase solution A obtained above solution B was now added at about 0° C., and stirring continued at room-temperature overnight. The organic phase was separated off and the aqueous phase extracted once with tert.-butylmethylether. The combined organic phases were washed with brine, dried and evaporated. The residual 2-hydroxy-pent-4-enenitrile obtained as liquid was stabilized by addition of a small amount of chloroacetic acid and used without further purification in the following step; $^1$H-NMR (CDCl$_3$): 5.85, m, 1H, 5.82, m, 2H, 4.53, t, 1H, 2.62, m, 2H.

B: 6.5 gr (67 mMol) 2-hydroxy-pent-4-enenitrile (prepared as in A above or following Tetr. 55, 1087 (1999)) was dissolved in dichloromethane (25 ml) and treated at –15° C. with 14 ml (100 mMol) triethylamine, followed by addition of 5.7 ml (74 mMol) methansulfochloride, where the temperature was held under cooling below +10° C. Stirring was continued until 25° C. was reached, and the reaction mixture was extracted with water against tert.-butylmethylether, washed with brine, dried and evaporated. Purification by flash chromatography (eluent: cyclohexane/ethylacetate 2:1) yielded as liquid methanesulfonic acid 1-cyano-but-3-enyl ester; $^1$H-NMR (CDCl$_3$): 5.81, m, 1H, 5.37, m, 2H, 5.21, t, 1H, 3.20, s, 3H, 2.76, m, 2H.

Example 14

This Example illustrates the pesticidal/insecticidal properties of compounds of formula (I). The compounds numbers are those of the characterising data tables. Tests against the following pests were performed as described below.

14.1 *Heliothis virescens* (Tobacco Budworm):

Eggs (0-24 h old) were placed in 24-well microtiter plate on artificial diet and treated with test solutions at an application rate of 200 ppm by pipetting. After an incubation period of 4 days, samples were checked for egg mortality, larval mortality, and growth regulation. The following compounds gave at least 80% control of *Heliothis virescens:* 1.054, 1.018, 1.033, 1.065, 1.046, 1.020, 1.044, 1.075, 1.024, 1.030, 1.031, 1.032, 1.068, 1.037, I-50, I-106, 1.053, 1.077, 1.021, 1.038, 1.062, 1.064, III-50, 1.048, III-106, 1.047, 1.025

14.2 *Myzus persicae* (Green Peach Aphid):

Sunflower leaf discs were placed on agar in a 24-well microtiter plate and sprayed with test solutions at an application rate of 200 ppm. After drying, the leaf discs were infested with an aphid population of mixed ages. After an incubation period of 6 DAT, samples were checked for mortality.

The following compounds gave at least 80% control of *Myzus persicae:* 1.012, I-50, I-106, I-126, III-50, 1.013, 1.043, 1.018, 1.019, 1.019, 1.020, 1.074, 1.075, 1.076, 1.023, 1.024, 1.025, 1.026, 1.029, 1.030, 1.031, 1.032, 1.045, 1.046, 1.047, 1.077, 1.033, 1.034, 1.035, 1.036, 1.048, 1.049, 1.053, 1.037, 1.038, 1.039, 1.068, 1.058, 1.059, 1.060, 1.062, 1.063, 1.065, 1.066, 1.069, 1.070, 1.071.

14.3 *Myzus persicae* (Green Peach Aphid):

Roots of pea seedlings, infested with an aphid population of mixed ages, were placed directly in the test solutions of 24 ppm. 6 days after introduction, samples were checked for mortality.

The following compounds gave at least 80% control of *Myzus persicae*: III-50, 1.076, 1.029, 1.043, 1.025, 1.030, 1.032, 1.046, 1.047, 1.034, 1.035, 1.048, 1.049, 1.053, I-106, I-126, III-50, 1.019, 1.075, 1.025, 1.030, 1.030, 1.031, 1.032, 1.049, 1.053, 1.038, 1.068, 1.059, 1.065, 1.013, 1.019, I-126, I-106, 1.019, 1.075, 1.025, 1.030, 1.031, 1.033, 1.036, 1.013, 1.046, 1.047, 1.036, 1.048.

14.4 *Tetranychus urticae* (Two-spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compounds gave at least 80% control of *Tetranychus urticae*: I-50, I-106, I-126, III-106, 1.041, 1.042, 1.043, 1.044, 1.045, 1.046, 1.047, 1.048, 1.049, 1.050, 1.051, 1.059, 1.060, 1.062, 1.064, 1.065.

The invention claimed is:

1. A compound of formula (I)

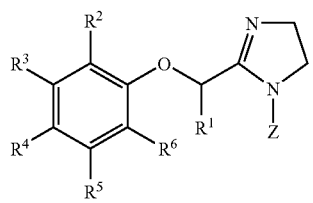

or salt or N-oxide thereof, wherein:

$R^1$ is:

(i) a $C_{1-6}$ alkyl substituted with one or more of hydroxyl; cyano; optionally substituted $C_{3-6}$ cycloalkyl, said substitution being selected from one or more of halogen, cyano, $C_{1-3}$ haloalkyl and $C_{1-3}$ alkoxy; optionally substituted pyridyl, said substitution being selected from one or more of halogen, cyano, $C_{1-3}$ alkyl, $C_{1-3}$ haloalkyl and $C_{1-3}$ alkoxy; optionally substituted pyrimidinyl, said substitution being selected from one or more of halogen, cyano, $C_{1-3}$ alkyl, $C_{1-3}$ haloalkyl and $C_{1-3}$ alkoxy; optionally substituted furyl, said substitution being selected from one or more of halogen, cyano, $C_{1-3}$ alkyl, $C_{1-3}$ haloalkyl and $C_{1-3}$ alkoxy; optionally substituted thienyl, said substitution being selected from halogen, cyano, $C_{1-3}$ alkyl, $C_{1-3}$ haloalkyl and $C_{1-3}$ alkoxy; tetrahydrofuryl optionally substituted with $C_{1-3}$ alkyl or $C_{1-3}$ alkoxy; tetrahydropyranyl optionally substituted with $C_{1-3}$ alkyl or $C_{1-3}$ alkoxy; 1,3-dioxolanyl optionally substituted with $C_{1-3}$ alkyl or $C_{1-3}$ alkoxy; $C_{1-3}$ alkoxy; $C_{1-3}$ haloalkoxy; allyloxy; propargyloxy; $C_{1-3}$ alkylthio; $C_{1-3}$ alkylsulfinyl; $C_{1-3}$ alkylsulfonyl; formyl; $C_{1-3}$ alkylcarbonyl; cyclopropylcarbonyl; $C_{1-3}$ haloalkylcarbonyl; $C_{1-3}$ alkoxycarbonyl; $C_{1-3}$ alkylthiocarbonyl; aminocarbonyl; $C_{1-3}$ alkylaminocarbonyl; N,N-di-($C_{1-3}$ alkyl)aminocarbonyl; amino; $C_{1-3}$ alkylamino; di ($C_{1-3}$ alkyl)amino; formylamino; $C_{1-3}$ alkylcarbonylamino; $C_{1-3}$ haloalkylcarbonylamino; $C_{1-3}$ alkylsulfonylamino; $C_{1-3}$ haloalkylsulfonylamino; $C_{1-3}$ alkylcarbonyloxy; $C_{1-3}$ haloalkylcarbonyloxy; cyclopropylcarbonyloxy; benzoyloxy; $C_{1-3}$ alkoxycarbonylamino; $C_{1-3}$ alkoxycarbonyloxy; or $C_{1-3}$ alkylcarbonylthio; or (ii) a $C_{2-6}$ alkenyl, optionally substituted with one or more of halogen; cyano; $C_{3-6}$ cycloalkyl optionally substituted with one or more of halogen and $C_{1-3}$ alkoxy; $C_{1-3}$ alkoxy; $C_{1-3}$ haloalkoxy; $C_{1-3}$ alkylthio; $C_{1-3}$ haloalkylthio; $C_{1-3}$ alkylsulfinyl; $C_{1-3}$ alkylsulfonyl; $C_{1-3}$ alkylcarbonyl; $C_{1-3}$ alkoxycarbonyl; aminocarbonyl; $C_{1-3}$ alkylaminocarbonyl; N,N-di-($C_{1-3}$ alkyl)aminocarbonyl; amino; $C_{1-3}$ alkylamino; formylamino; $C_{1-3}$ alkylcarbonylamino; $C_{1-3}$ haloalkylcarbonylamino; or $C_{1-3}$ alkylsulfonylamino; or (iii) $C_{3-6}$ cycloalkyl optionally substituted with one or more of halogen, $C_{1-3}$ alkyl, $C_{1-3}$ haloalkyl, or $C_{1-3}$ alkoxy; or (iv) $C_{3-6}$ cycloalkenyl optionally substituted with one or more of halogen, $C_{1-3}$ alkyl, $C_{1-3}$ haloalkyl, or $C_{1-3}$ alkoxy; or (v) $C_{2-6}$ alkynyl optionally substituted with one or more of halogen, hydroxyl, cyano, $C_{1-3}$ alkoxy, $C_{1-3}$ haloalkoxy, or $C_{1-3}$ alkylthio;

$R^2$ is methyl, ethyl, $C_{1-2}$ haloalkyl or halogen;

$R^3$ is hydrogen, methyl, ethyl, $C_{1-2}$ haloalkyl or halogen;

$R^4$ is hydrogen, methyl or halogen;

$R^5$ is hydrogen, methyl or halogen;

$R^6$ is hydrogen, methyl, ethyl, or halogen;

Z is hydrogen;

G is optionally substituted $C_{1-10}$ alkyl, optionally substituted $C_{2-6}$ alkenyl, optionally substituted $C_{2-6}$ alkynyl, optionally substituted $C_{3-7}$ cycloalkyl, optionally substituted $C_{3-7}$ cycloalkenyl, optionally substituted aryl, optionally substituted heteroaryl or optionally substituted heterocyclyl;

A is S(O), $SO_2$, C(O) or C(S);

$R^7$, $R^8$ and $R^9$ are each independently hydrogen or G; or $R^7$ and $R^8$ together with the N atom to which they are attached form a group N=$CR^{12}R^{13}$; or $R^7$ and $R^8$ together with the N atom to which they are attached form a five, six or seven-membered heterocyclic ring optionally containing one or two additional heteroatoms selected from O, N or S, and optionally substituted by one or two $C_{1-6}$ alkyl groups;

$R^{10}$ and $R^{11}$ are each independently $C_1$-$C_6$ alkyl, benzyl or phenyl wherein the phenyl group is optionally substituted with halogen, nitro, cyano, $C_{1-3}$ alkyl, $C_{1-3}$ haloalkyl, $C_{1-3}$ alkoxy, or $C_{1-3}$ haloalkoxy;

$R^{12}$, $R^{13}$, $R^{14}$, $R^{15}$, $R^{16}$ and $R^{17}$ are each independently hydrogen or $C_1$-$C_6$ alkyl; and X is O or S, with the proviso that the compound of formula (I) is not 3-(4,5-dihydro-1H-imidazol-2-yl)-3-(2,6-dimethyl-phenoxy)-propan-1-ol.

2. The compound according to claim 1 wherein $R^2$ and $R^3$ are each independently methyl, fluoromethyl, difluoromethyl, trifluoromethyl, fluoro, or chloro.

3. The compound according to claim 2 wherein $R^2$ and $R^3$ are each independently methyl, trifluoromethyl, difluoromethyl, fluoro or chloro; and $R^4$, $R^5$ and $R^6$ are each independently hydrogen or fluoro.

4. The compound according to claim 3 wherein $R^4$, $R^5$ and $R^6$ are each hydrogen.

5. A process for the preparation of a compound of the formula (I) as defined in claim 1, which comprises reacting a compound of formula (4)

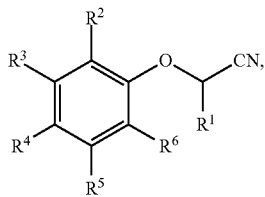

(4)

wherein $R^1$, $R^2$, $R^3$, $R^4$, $R^5$ and $R^6$ are as defined above, with a diamine of formula (5)

$$H_2N-C_2H_4-NHZ \quad (5),$$

wherein Z is as defined above, in the presence of a catalyst.

6. A compound of formula (4)

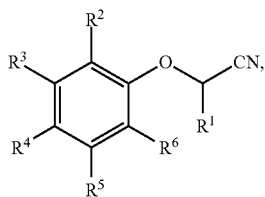

(4)

wherein:
$R^1$ is:
(i) a $C_{1-6}$ alkyl substituted with one or more of hydroxyl; cyano; optionally substituted $C_{3-6}$ cycloalkyl, said substitution being selected from one or more of halogen, cyano, $C_{1-3}$ haloalkyl and $C_{1-3}$ alkoxy; optionally substituted pyridyl, said substitution being selected from one or more of halogen, cyano, $C_{1-3}$ alkyl, $C_{1-3}$ haloalkyl and $C_{1-3}$ alkoxy; optionally substituted pyrimidinyl, said substitution being selected from one or more of halogen, cyano, $C_{1-3}$ alkyl, $C_{1-3}$ haloalkyl and $C_{1-3}$ alkoxy; optionally substituted furyl, said substitution being selected from one or more of halogen, cyano, $C_{1-3}$ alkyl, $C_{1-3}$ haloalkyl and $C_{1-3}$ alkoxy; optionally substituted thienyl, said substitution being selected from halogen, cyano, $C_{1-3}$ alkyl, $C_{1-3}$ haloalkyl and $C_{1-3}$ alkoxy; tetrahydrofuryl optionally substituted with $C_{1-3}$ alkyl or $C_{1-3}$ alkoxy; tetrahydropyranyl optionally substituted with $C_{1-3}$ alkyl or $C_{1-3}$ alkoxy; 1,3-dioxolanyl optionally substituted with $C_{1-3}$ alkyl or $C_{1-3}$ alkoxy; $C_{1-3}$ alkoxy; $C_{1-3}$ haloalkoxy; allyloxy; propargyloxy; $C_{1-3}$ alkylthio; $C_{1-3}$ alkylsulfinyl; $C_{1-3}$ alkylsulfonyl; formyl; $C_{1-3}$ alkylcarbonyl; cyclopropylcarbonyl; $C_{1-3}$ haloalkylcarbonyl; $C_{1-3}$ alkoxycarbonyl; $C_{1-3}$ alkylthiocarbonyl; aminocarbonyl; $C_{1-3}$ alkylaminocarbonyl; N,N-di-($C_{1-3}$ alkyl)aminocarbonyl; amino; $C_{1-3}$ alkylamino; di ($C_{1-3}$ alkyl)amino; formylamino; $C_{1-3}$ alkylcarbonylamino; $C_{1-3}$ haloalkylcarbonylamino; $C_{1-3}$ alkylsulfonylamino; $C_{1-3}$ haloalkylsulfonylamino; $C_{1-3}$ alkylcarbonyloxy; $C_{1-3}$ haloalkylcarbonyloxy; cyclopropylcarbonyloxy; benzoyloxy; $C_{1-3}$ alkoxycarbonylamino; $C_{1-3}$ alkoxycarbonyloxy; or $C_{1-3}$ alkylcarbonylthio; or (ii) a $C_{2-6}$ alkenyl, optionally substituted with one or more of halogen; cyano; $C_{3-6}$ cycloalkyl optionally substituted with one or more of halogen and $C_{1-3}$ alkoxy; $C_{1-3}$ alkoxy; $C_{1-3}$ haloalkoxy; $C_{1-3}$ alkylthio; $C_{1-3}$ haloalkylthio; $C_{1-3}$ alkylsulfinyl; $C_{1-3}$ alkylsulfonyl; $C_{1-3}$ alkylcarbonyl; $C_{1-3}$ alkoxycarbonyl; aminocarbonyl; $C_{1-3}$ alkylaminocarbonyl; N,N-di-($C_{1-3}$ alkyl)aminocarbonyl; amino; $C_{1-3}$ alkylamino; formylamino; $C_{1-3}$ alkylcarbonylamino; $C_{1-3}$ haloalkylcarbonylamino; or $C_{1-3}$ alkylsulfonylamino; or (iii) $C_{3-6}$ cycloalkyl optionally substituted with one or more of halogen, $C_{1-3}$ alkyl, $C_{1-3}$ haloalkyl, or $C_{1-3}$ alkoxy; or (iv) $C_{3-6}$ cycloalkenyl optionally substituted with one or more of halogen, $C_{1-3}$ alkyl, $C_{1-3}$ haloalkyl, or $C_{1-3}$ alkoxy; or (v) $C_{2-6}$ alkynyl optionally substituted with one or more of halogen, hydroxyl, cyano, $C_{1-3}$ alkoxy, $C_{1-3}$ haloalkoxy, or $C_{1-3}$ alkylthio;

$R^2$ is methyl, ethyl, $C_{1-2}$ haloalkyl or halogen;
$R^3$ is hydrogen, methyl, ethyl, $C_{1-2}$ haloalkyl or halogen;
$R^4$ is hydrogen, methyl or halogen;
$R^5$ is hydrogen, methyl or halogen; and
$R^6$ is hydrogen, methyl, ethyl, or halogen.

7. An insecticidal, acaricidal, nematicidal or molluscicidal composition comprising (i) a compound according to claim 1 or (ii) 3-(4,5-dihydro-1H-imidazol-2-yl)-3-(2,6-dimethylphenoxy)-propan-1-ol, and (iii) a suitable inert diluent or carrier.

8. A method of combating a pest selected from the group consisting of insects, acarids, nematodes and molluscs, which comprises applying to said pest, or to the locus of said pest, or to a plant susceptible to attack by said pest, a pesticidally effective amount of (i) a compound according to claim 1, or (ii) 3-(4,5-dihydro-1H-imidazol-2-yl)-3-(2,6-dimethyl-phenoxy)-propan-1 -ol.

9. The method according to claim 8, wherein said pest is an insect of the order Hemiptera, Lepidoptera, Coleoptera, Thysanoptera, Diptera, Blattodea, Isoptera, Siphonaptera, Hymenoptera, or Orthoptera.

10. The method according to claim 9, wherein said insect is of the order Hemiptera, Lepidoptera, Coleoptera, Thysanoptera, or Diptera.

11. The method according to claim 10, wherein said insect is of the order Hemiptera.

12. The method according to claim 9, wherein said insect is of the order Lepidoptera, Thysanoptera, Isoptera, Siphonaptera, Hymenoptera, or Orthoptera.

13. The method according to claim 8 wherein said pest is an acarid.

14. The compound according to claim 1 wherein $R^1$ is $C_{1-3}$ alkyl substituted with cyano, cyclopropyl, $C_{1-3}$ alkoxy, allyloxy, propargyloxy, $C_{1-3}$ alkylthio, $C_{1-3}$ alkylsulfinyl, $C_{1-3}$ alkylsulfonyl, formyl, $C_{1-3}$ alkylcarbonyl, cyclopropylcarbonyl, $C_{1-3}$ haloalkylcarbonyl, $C_{1-3}$ alkoxycarbonyl, $C_{1-3}$ alkylthiocarbonyl, aminocarbonyl, $C_{1-3}$ alkylaminocarbonyl, N,N-di-($C_{1-3}$ alkyl)aminocarbonyl, $C_{1-3}$ alkylcarbonyloxy, $C_{1-3}$ haloalkylcarbonyloxy, cyclopropylcarbonyloxy, benzoyloxy, or $C_{1-3}$ alkoxycarbonyloxy.

15. The compound according to claim 14 wherein $R^1$ is $C_{1-3}$ alkyl substituted with cyano, cyclopropyl, or $C_{1-2}$ alkoxy.

16. The compound according to claim 1 wherein $R^1$ is $C_{2-4}$ alkenyl, optionally substituted with halogen, cyano, $C_{1-3}$ alkoxy, $C_{1-3}$ haloalkoxy, $C_{1-3}$ alkylthio, $C_{1-3}$ haloalkylthio, $C_{1-3}$ alkylsulfinyl, $C_{1-3}$ alkylsulfonyl, $C_{1-3}$ alkylcarbonyl, or $C_{1-3}$ alkoxycarbonyl; or $C_{2-4}$ alkynyl optionally substituted with halogen, cyano, or $C_{1-3}$ alkoxy.

17. The compound according to claim 16 wherein $R^1$ is $C_{2-4}$ alkenyl substituted with halogen, cyano, $C_{1-3}$ alkoxy, $C_{1-3}$ haloalkoxy, $C_{1-3}$ alkylthio, $C_{1-3}$ haloalkylthio, $C_{1-3}$ alkylsulfinyl, $C_{1-3}$ alkylsulfonyl, $C_{1-3}$ alkylcarbonyl, or $C_{1-3}$ alkoxycarbonyl; or $C_{2-4}$ alkynyl substituted with halogen, cyano, or $C_{1-3}$ alkoxy.

18. The compound according to claim 3 wherein $R^1$ is $C_{1-3}$ alkyl substituted with cyano, cyclopropyl, or $C_{1-2}$ alkoxy.

* * * * *